United States Patent
Hajko et al.

(10) Patent No.: US 7,608,714 B2
(45) Date of Patent: Oct. 27, 2009

(54) PRODUCTION OF DOLASETRON

(75) Inventors: Janos Hajko, Debrecen (HU); Tivadar Tamas, Debrecen (HU); Adrienne Kovacsne-Mezei, Debrecen (HU); Erika Magyar Molnarne, Debrecen (HU); Csaba Peto, Debrecen (HU); Csaba Szabo, Debrecen (HU)

(73) Assignee: TEVA Gyógyszergyár Zártkörúen Müködö Részvénytársaság, Debrecen (HU)

( * ) Notice: Subject to any disclaimer, the term of this patent is extended or adjusted under 35 U.S.C. 154(b) by 130 days.

(21) Appl. No.: 11/650,294

(22) Filed: Jan. 5, 2007

(65) Prior Publication Data

US 2007/0203219 A1   Aug. 30, 2007

Related U.S. Application Data

(60) Provisional application No. 60/756,690, filed on Jan. 5, 2006, provisional application No. 60/800,884, filed on May 15, 2006, provisional application No. 60/838,758, filed on Aug. 17, 2006, provisional application No. 60/861,354, filed on Nov. 27, 2006, provisional application No. 60/802,842, filed on May 22, 2006, provisional application No. 60/818,934, filed on Jul. 5, 2006, provisional application No. 60/833,515, filed on Jul. 24, 2006, provisional application No. 60/836,432, filed on Aug. 7, 2006, provisional application No. 60/763,683, filed on Jan. 30, 2006, provisional application No. 60/784,248, filed on Mar. 20, 2006, provisional application No. 60/815,199, filed on Jun. 19, 2006, provisional application No. 60/852,887, filed on Oct. 18, 2006.

(51) Int. Cl.
C07D 221/22 (2006.01)
C07D 451/00 (2006.01)
C07D 455/00 (2006.01)

(52) U.S. Cl. .......................................... 546/72; 546/94
(58) Field of Classification Search .................. 546/72, 546/94

See application file for complete search history.

(56) References Cited

U.S. PATENT DOCUMENTS 4,906,755 A * 3/1990 Gittos .......................... 546/94
5,011,846 A * 4/1991 Gittos et al. ................. 514/294

FOREIGN PATENT DOCUMENTS

| EP | 0 266 730 A1 | 11/1988 |
|----|--------------|---------|
| EP | 0 329 905 A1 | 8/1989 |
| EP | 0 330 788 A1 | 9/1989 |
| EP | 0 330 824 A1 | 9/1989 |
| EP | 0 330-824 A1 | 9/1989 |
| EP | 0 339 669 A1 | 11/1989 |
| EP | 339669 * | 11/1989 |
| EP | 0 517 984 A1 | 12/1992 |
| WO | WO-96/28402 A1 | 9/1996 |
| WO | WO-2006/026927 A1 | 3/2006 |
| WO | WO-2006/056081 A1 | 6/2006 |
| WO | WO-2007/003522 A1 | 1/2007 |
| WO | WO-2007/003522 A1 | 1/2007 |
| WO | WO-2007/072506 A2 | 6/2007 |
| WO | WO-2007/072507 A2 | 6/2007 |

OTHER PUBLICATIONS

Corey, E.J. et al. "Protection of Hydroxyl Groups as *tert*-Butyldimethylsilyl Derivatives", Journal of the American Chemical Society, Aug. 23, 1972, vol. 94, No. 17, pp. 6190-6191.

Martinez, Luis E., et al., "Highly Effective and Enantioselective Synthesis of Carbocyclic Nucleoside Analogs Using Selective Early Transition Metal Catalysis", Journal of Organic Chemistry, 1996, vol. 61, pp. 7963-7966.

Database Crossfire, Beilstein Institut zur Foerderung der Chemischen Wissenschaften, XP-002441386, Database accession No. 9139751, Abstract. (1988-2007).

Database Crossfire, Beilstein Institut zur Foerderung der Chemischen Wissenschaften, XP-002441387, Database accession No. 747184, Abstract. (1988-2007).

Gu, Chong-Hui, et al., "Grouping solvents by statistical analysis of solvent property parameters: implication to polymorph screening", International Journal of Pharmaceutics, Sep. 28, 2004, vol. 283, pp. 117-125.

* cited by examiner

*Primary Examiner*—D. Margaret Seaman
*Assistant Examiner*—Niloofar Rahmani
(74) *Attorney, Agent, or Firm*—Kenyon & Kenyon LLP

(57) ABSTRACT

The present invention provides an improved process for the preparation of Dolasetron salts, in particularly Dolasetron mesylate. Also provided are intermediates for the process and methods of preparing the intermediates.

80 Claims, 8 Drawing Sheets

PRODUCTION OF DOLASETRON

CROSS REFERENCE TO RELATED APPLICATIONS

The present application claims the benefit of the following U.S. Provisional Patent Application Nos.: 60/756,690, filed Jan. 5, 2006; 60/800,884, filed May 15, 2006; 60/838,758, filed Aug. 17, 2006; 60/861,354, filed Nov. 27, 2006; 60/802,842, filed May 22, 2006; 60/818,934, filed Jul. 5, 2006; 60/833,515, filed Jul. 24, 2006; 60/836,432, filed Aug. 7, 2006; 60/763,683, filed Jan. 30, 2006; 60/784,248, filed Mar. 20, 2006; 60/815,199, filed Jun. 19, 2006; 60/852,887, filed Oct. 18, 2006. The contents of these applications are incorporated herein by reference.

FIELD OF THE INVENTION

The present invention relates to an improved process for the preparation of Dolasetron salts, in particularly Dolasetron mesylate, and intermediates thereof.

BACKGROUND OF THE INVENTION

Dolasetron mesylate monohydrate, $(2\alpha,6\alpha,8\alpha,9\alpha\beta)$-octahydro-3-oxo-2,6-methano-2H-quinolizin-8-yl-1H-indole-3-carboxylate monomethanesulfonate monohydrate, (referred to as DLS-MsOH-H$_2$O) a compound having the chemical structure,

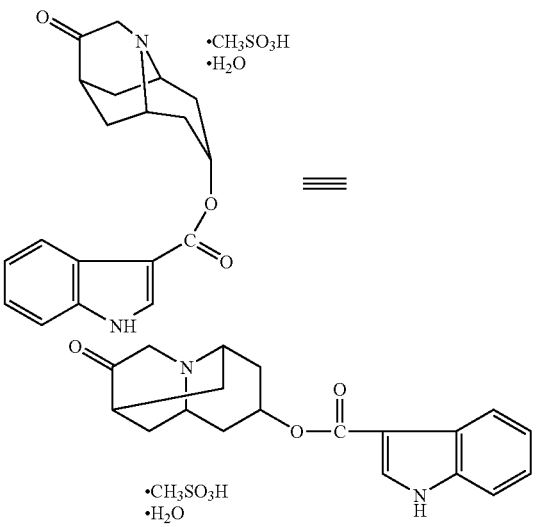

Dolasetron Mesylate monohydrate is a serotonin receptor (5-HT$_3$) antagonist used as an antiemetic and antinauseant agent in chemo- and radiotherapies.

DLS-MsOH-H$_2$O developed by Merrell Dow Pharmaceuticals is marketed as tablets for oral administration and as sterile solution for intravenous administration by Aventis, under the name Anzemet®.

DLS-MsOH and its monohydrate form can be prepared by a multi step synthesis, as described in EP patent No. 0339669 ("the EP '669 patent") as illustrated in the following scheme

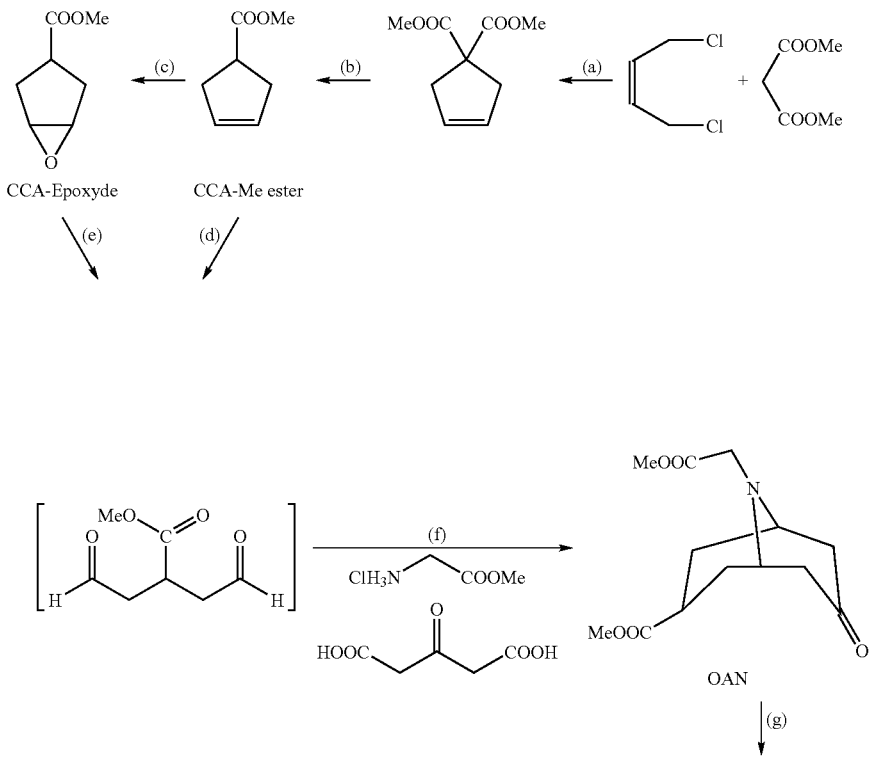

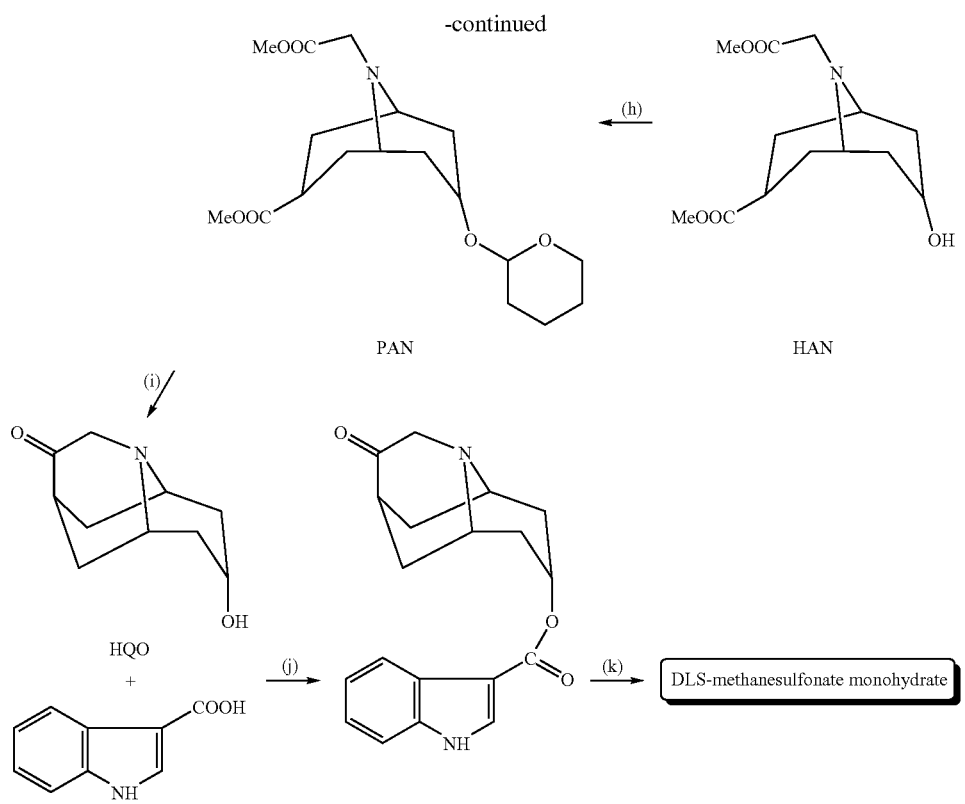

Accordingly, step (c) of the reaction involves oxidation with a molar equivalent of an expensive oxidizing reagent, 3-chloroperbenzoic acid (referred to as mCPBA), which transforms to 3-chlorobenzoic acid (referred to as mCBA), waste that is disposed at the end of the reaction. Removal of mCBA is problematic, hence, leading to a contaminated product. CCA-epoxide is also contaminated by other aromatic impurities, such as [(3-ClPh)C(O)O]$_2$ (the corresponding peroxide ) in an amount of 5%. Therefore, the oxidation reaction as described above is non-economic for scale-up. Also, the reaction in steps (e) and (f) are done by using periodic acid in ethyl acetate in step (e), and water as a solvent in step (f). Since, the reagents and the reduction products have low solubility in ethylacetate; the reaction disclosed in the above patent is slower. Also, the reaction in ethylacetate is more dangerous. In addition, since two different solvents are used in steps (e) and (f), a work-up procedure, which can lead to a decomposition of the sensitive 3-methoxycarbonyl-1,5-glutardialdehyde (the product of the oxidation step), is required.

A similar process is apparently described in EP patent No. 0266730, comprising an oxidation reaction, as described in step (c) of the above scheme, to the corresponding diol, instead of to the epoxide, as apparently disclosed in EP patent No. 0339669. The diol is then transformed to DLS-base in a similar way.

Hence, there is a need in the art for an improved process for the preparation of Dolasetron salts, preferably, Dolasetron Mesylate.

SUMMARY OF THE INVENTION

In one embodiment, the present invention provides a 7-alkoxycarbonyl-9-(alkoxycarbonylmethyl)-3-[(tetrahydro-2H-pyran2-yl)oxy]-9-azabicyclo[3.3.1]nonane compound (referred to as a PAN compound) of formula VII;

VII

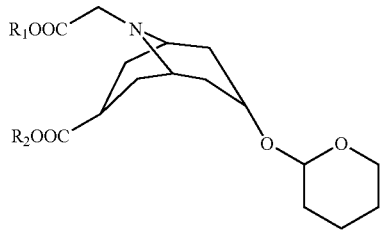

wherein $R_1$, and $R_2$ are described before.

In another embodiment, the present invention provides crystalline 7-methoxycarbonyl-9-(methoxycarbonylmethyl)-3-[(tetrahydro-2H-pyran2-yl)oxy]-9-azabicyclo[3.3.1]nonane (referred to as PAN).

In one embodiment, the present invention provides a quaternary ammonium salt of a 7-alkoxycarbonyl-9-(alkoxycarbonylmethyl)-3-[(tetrahydro-2H-pyran2-yl)oxy]-9-azabicyclo[3.3.1]nonane compound (referred to as a PAN-salt) of formula VIIs;

VIIs

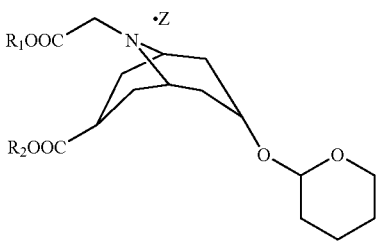

wherein $R_1$, $R_2$ and Z are described before.

In another embodiment, the present invention provides crystalline methanesulfonate salt of 7-methoxycarbonyl-9-(methoxycarbonylmethyl)-3-[(tetrahydro-2H-pyran2-yl)oxy]-9-azabicyclo[3.3.1]nonane (referred to as PAN-MsOH).

In yet another embodiment, the present invention provides an isolated endo-9-alkoxycarbonyl-5-[(tetrahydro-2H-pyran-2-yl)oxy]-8-azatricyclo[5.3.1.0$^{3,8}$]undecan-10-one (trans-hexahydro-4-alkoxycarbonyl-8-[(tetrahydro-2H-pyran-2-yl)oxy]-2,6-methano-2H-quinolizin-3(4H)-one) compound (referred to a PQO compound) of formula IX.

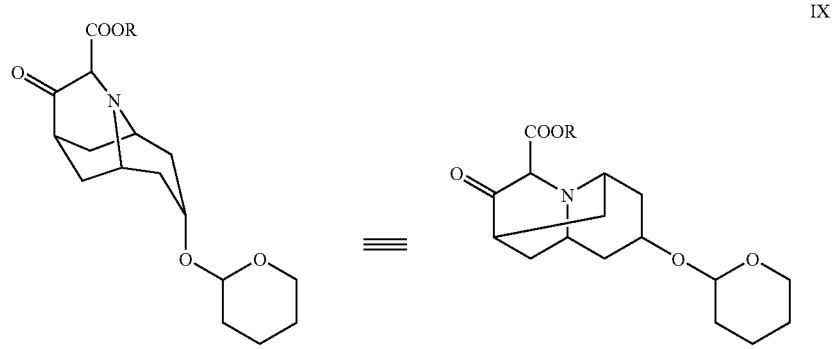

wherein R is a $C_{1-6}$ alkyl or a $C_{6-8}$ aryl, preferably, a $C_{1-4}$ alkyl, more preferably, methyl.

In another embodiment, the present invention provides crystalline endo-9-methoxycarbonyl-5-[(tetrahydro-2H-pyran-2-yl)oxy]-8-azatricyclo[5.3.1.0$^{3,8}$]undecan-10-one (trans-hexahydro-4-methoxycarbonyl-8-[(tetrahydro-2H-pyran-2-yl)oxy]-2,6-methano-2H-quinolizin-3(4H)-one) (referred to as PQO).

In one embodiment, the present invention provides a 7-alkoxycarbonyl-9-(alkoxycarbonylmethyl)-3-acyloxy-9-azabicyclo[3.3.1]nonane compound (referred to as a PivAN compound) of formula XIII;

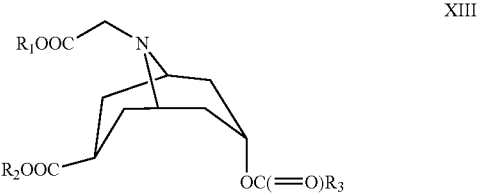

wherein $R_1$, $R_2$ and $R_3$ are independently a $C_{1-6}$ alkyl or a $C_{6-8}$ aryl, preferably, a $C_{1-4}$ alkyl, more preferably, $R_1$ and $R_2$ are methyl, and $R_3$ is tert-butyl.

In one embodiment, the present invention provides a process for the preparation of a 7-methoxycarbonyl-9-(methoxycarbonylmethyl)-3-[(tetrahydro-2H-pyran-2-yl)oxy]-9-azabicyclo[3.3.1]nonane compound (a PAN compound) of formula VII, comprising

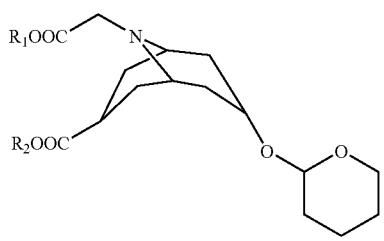

a) preparing a 7-alkoxycarbonyl-9-(alkoxycarbonylmethyl)-9-azabicyclo[3.3.1]nonane-3-ol compound (a HAN compound) of formula VI

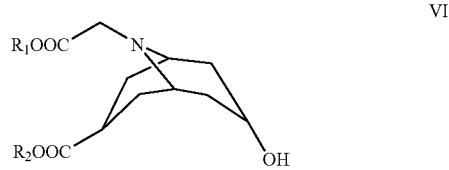

by a process comprising combining an OAN compound of formula V or salts thereof, a reducing agent, and a solvent selected from the group consisting of water, water miscible organic solvents and mixtures thereof to form mixture to obtain an HAN compound of formula VI;

b) mixing the HAN compound of formula VI, an ether protecting group, an acid, and a $C_{3-8}$ ester to form a mixture; and c) adding a base to the mixture to obtain the PAN compound of formula VII, wherein $R_1$ and $R_2$ are independently a $C_{1-6}$ alkyl or a $C_{6-8}$ aryl.

In one embodiment, the present invention provides a process for the preparation of a PQO compound of formula IX

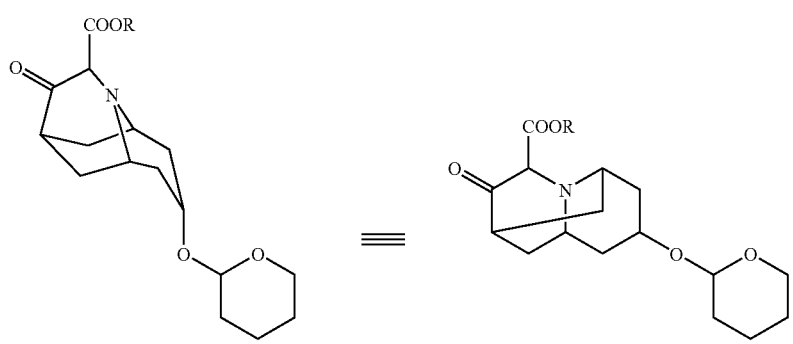

IX comprising a) combining a PAN compound of formula VII,

VII

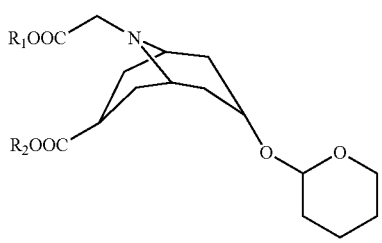

a metal alkoxide, and a polar a-protic organic solvent to form a mixture; b) heating the mixture; c) reacting the product of step b) with a weak acid forming a reaction mixture; and d) adding a base to the reaction mixture of step c), forming a PQO compound of formula IX; wherein, R, $R_1$ and $R_2$ are independently a $C_{1-6}$ alkyl or $C_{6-8}$ aryl, preferably, a $C_{1-4}$ alkyl, more preferably, methyl.

In yet another embodiment, the present invention provides a process for preparing a DLS-salt of formula VIIIs comprising preparing a PQO compound of formula IX by the process of the invention, and converting it to a DLS-salt of formula VIIIs.

In one embodiment, the present invention provides a process for the preparation of a HQO-salt of formula IIs IIs

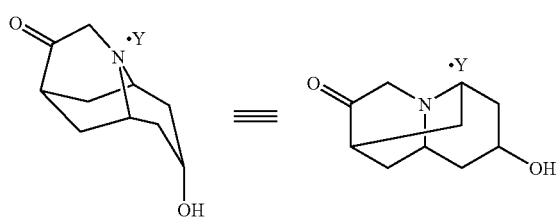

comprising combining a PAN compound of formula VII,

VII

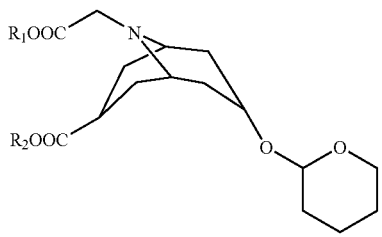

a metal alkoxide, and a polar aprotic organic solvent forming a mixture; and adding to the mixture an acid selected from the group consisting of: hydrochloric acid, hydrobromic acid, sulfuric acid, nitric acid, phosphoric acid, and perchloric acid, forming the HQO salt of formula IIs, wherein $R_1$ and $R_2$ are as described before, and Y is an acid selected from the group consisting of: hydrochloric acid, hydrobromic acid, sulfuric acid, nitric acid, phosphoric acid, and perchloric acid, preferably, HCl.

When Y is HCl, said compound of formula IIs refers to the hydrochloride salt of HQO (referred to as HQO-HCl) of the following formula.

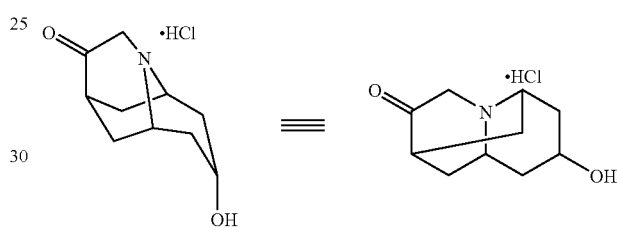

In yet another embodiment, the present invention provides a process for purifying HQO of formula II

II

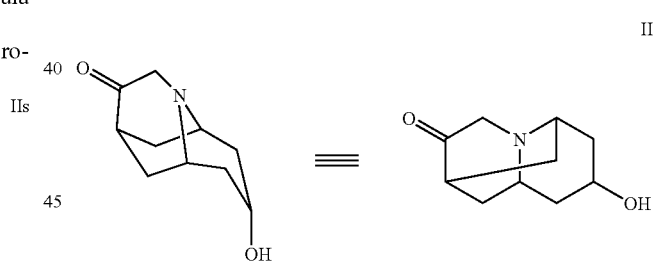

comprising combining a PAN compound of formula VII, a metal alkoxide, and a polar aprotic organic solvent, and reacting it with an acid selected from the group consisting of: hydrochloric acid, hydrobromic acid, sulfuric acid, nitric acid, phosphoric acid, perchloric acid, forming a reaction mixture; and adding a base to the reaction mixture, wherein $R_1$ and $R_2$ are as described before.

In yet another embodiment, the present invention provides another process for the preparation of a HQO-salt of formula IIs comprising combining HQO, an alcohol and an acid selected from the group consisting of: hydrochloric acid, hydrobromic acid, sulfuric acid, nitric acid, phosphoric acid, perchloric acid, fluoroboric acid, formic acid, acetic acid, propionic acid, trichloroacetic acid, trifluoroacetic acid, maleic acid, fumaric acid, succinic acid, oxalic acid, tartaric acid, citric acid, mandelic acid, benzoic acid, salicylic acid, naphthalene carboxylic and dicarboxylic acids, methanesulfonic acid, ethanesulfonic acid, trifluoromethanesulfonic acid, p-toluenesulfonic acid, benzenesulfonic acid, naphthalene sulfonic, and disulfonic acids, forming a HQO salt of formula IIs.

In one embodiment, the present invention provides a process for purifying HQO of formula II comprising a) combining HQO of formula II, an alcohol and an acid selected from the group consisting of: hydrochloric acid, hydrobromic acid, sulfuric acid, nitric acid, phosphoric acid, perchloric acid, fluoroboric acid, formic acid, acetic acid, propionic acid, trichloroacetic acid, trifluoroacetic acid, maleic acid, fumaric acid, succinic acid, oxalic acid, tartaric acid, citric acid, mandelic acid, benzoic acid, salicylic acid, naphthalene carboxylic and dicarboxylic acids, methanesulfonic acid, ethanesulfonic acid, trifluoromethanesulfonic acid, p-toluenesulfonic acid, benzenesulfonic acid, naphthalene sulfonic, and disulfonic acids; and b) adding a base, to obtain a purified HQO of formula II.

In one embodiment, the present invention provides a process for the preparation of a DLS-salt of formula VIIIs, comprising preparing a HQO-salt of formula IIs by the process of the invention, and converting it to a DLS-salt of formula VIIIs.

In another embodiment, the present invention provides a process for the preparation of a DLS-salt of formula VIIIs, comprising the steps of a) combining a CCA-ester of formula III, an oxidizing agent selected from the group consisting of: hydroperoxides, dialkyl peroxides, peroxyacids, peroxyesters, diacyl peroxides, persulphate, perborate and perphosphate, a catalyst and a solvent selected from the group consisting of water, water miscible organic solvents and mixtures thereof, to form a first intermediate mixture; b) adding an oxidizing agent, a solvent selected from the group consisting of water, and a water miscible organic solvent, to the first intermediate mixture forming a second intermediate mixture; c) raising the pH of the second intermediate mixture; d) reacting the products in the second intermediate mixture with a pH 4 buffer, a glycine $C_{1-4}$ ester or salts thereof, and a substance comprising a carbonyl moiety selected from the group consisting of 1,3-acetonedicarboxylic acids, acetone and a $C_{1-4}$ ester thereof, forming a third intermediate mixture; e) adding to the third intermediate mixture a reducing agent, and a solvent selected from the group consisting of water, water miscible organic solvents and mixtures thereof, forming a fourth intermediate mixture; f) mixing the fourth intermediate mixture with an ether protecting group, an acid, and a $C_{3-8}$ ester forming a fifth intermediate mixture; g) adding a base to the fifth intermediate mixture; h) further combining the fifth intermediate mixture with a metal alkoxide and a polar aprotic organic solvent forming a sixth intermediate mixture; i) heating the sixth intermediate mixture; j) adding to the sixth intermediate mixture an acid selected from the group consisting of: hydrochloric acid, hydrobromic acid, sulfuric acid, nitric acid, phosphoric acid, and perchloric acid forming a seventh intermediate mixture; k) adding a base to the seventh intermediate mixture; l) further mixing the seventh intermediate mixture with an anhydride, 3-indole carboxylic acid, a halogenated hydrocarbon, and a catalyst; and m) reacting the product of step l) with an acid to obtain the DLS-salt of formula VIIIs.

In another embodiment the above process of preparing a DLS-salt of formula VIIIs comprises the same steps as the process above wherein the steps g) and k) are optional.

In another embodiment, the present invention also provides a process for the preparation of a PivAN compound of formula XIII

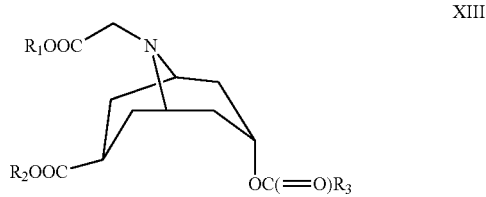

comprising combining a HAN compound of formula VI,

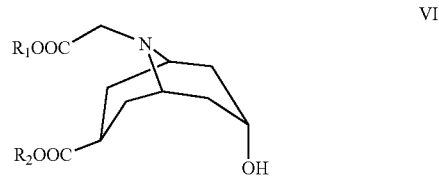

an acylating agent selected from a group consisting of: carboxylic acid, carboxylic halogenides, and carboxylic anhydrides, a base, and a solvent selected from the group consisting of a-protic organic solvents and mixtures thereof, to obtain a PivAN compound of formula XIII, wherein, $R_1$ and $R_2$ and $R_3$ are independently a $C_{1-6}$ alkyl or a $C_{6-8}$ aryl, preferably, a $C_{1-4}$ alkyl, more preferably, $R_1$ and $R_2$ are methyl and $R_3$ is tert-butyl.

In yet another embodiment, the present invention provides a process for the preparation of a DLS-salt of formula VIIIs, comprising preparing a PivAN compound of formula XIII by the process of the invention, and converting it to a DLS-salt of formula VIIIs.

In another embodiment, the present invention further provides a process for the preparation of HQO of formula II

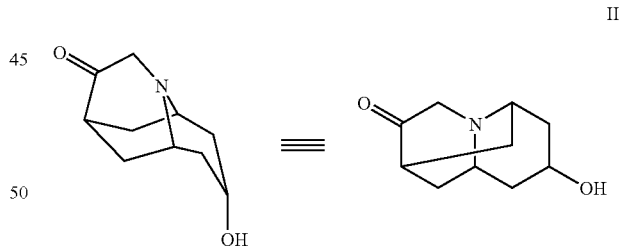

comprising combining a PivAN compound of formula XIII,

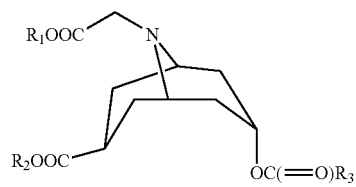

a metal alkoxide, and a polar aprotic organic solvent forming a mixture; heating the mixture; and adding to the mixture an acid selected from the group consisting of: hydrochloric acid, hydrobromic acid, sulfuric acid, nitric acid, phosphoric acid, and perchloric acid, preferably HCl, to obtain HQO of formula II.

In yet another embodiment, the present invention provides a process for the preparation of a DLS-salt of formula VIIIs, comprising preparing HQO of formula II from a PivAN compound of formula XIII by the process of the invention, and converting it to a DLS-salt of formula VIIIs.

The present invention also provides a process for preparing a DLS-salt of formula VIIIs, designated process No. 2, comprising a) combining a CCA-ester of formula III, an oxidizing agent selected from the group consisting of: hydroperoxides, dialkyl peroxides, peroxyacids, peroxyesters, diacyl peroxides, persulphate, perborate and perphosphate, a catalyst and a solvent selected from the group consisting of water, water miscible organic solvents and mixtures thereof, forming a first intermediate mixture; b) adding to the first intermediate mixture an oxidizing agent, a solvent selected from the group consisting of water and water miscible organic solvent, to form a second intermediate mixture; c) raising the pH of the second intermediate mixture; d) reacting the products in the second intermediate mixture with a pH 4 buffer, a glycine $C_{1-4}$ ester or salts thereof, and a substance comprising a carbonyl moiety selected from the group consisting of 1,3 acetonedicarboxylic acids, acetone and a $C_{1-4}$ ester thereof to form a third intermediate mixture; e) adding to the third intermediate mixture a reducing agent, and a solvent selected from the group consisting of water, water miscible organic solvents and mixtures thereof, to form a fourth intermediate mixture; f) adding to the fourth intermediate mixture an acylating agent selected from the group consisting of: carboxylic acid, carboxylic halogenides, and carboxylic anhydrides, a base, and a solvent selected from the group consisting of aprotic organic solvents and mixtures thereof, to form a fifth intermediate mixture; g) adding to the fifth intermediate mixture a metal alkoxide, and a polar aprotic organic solvent to form a sixth intermediate mixture; h) heating the sixth intermediate mixture, and adding an acid selected from the group consisting of: hydrochloric acid, hydrobromic acid, sulfuric acid, nitric acid, phosphoric acid, and perchloric acid to form a seventh intermediate mixture; i) mixing the seventh intermediate mixture with an anhydride, 3-indole carboxylic acid, a halogenated hydrocarbon, and a catalyst; and j) reacting the product of step i) with an acid to obtain the DLS-salt of formula VIIIs.

DETAILED DESCRIPTION OF THE INVENTION

The present invention offers novel intermediates in the syntheses of Dolasetron salts, especially, the mesylate salt, and processes for preparing them. The invention also offers the use of these intermediates in novel processes for preparing Dolasetron salts, especially, the mesylate salt.

The present invention further provides a 7-alkoxycarbonyl-9-(alkoxycarbonylmethyl)-3-[(tetrahydro-2H-pyran2-yl)oxy]-9-azabicyclo[3.3.1]nonane compound (referred to as a PAN compound) of formula VII;

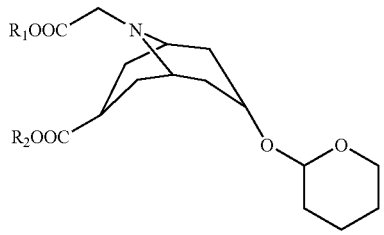

VII wherein $R_1$, and $R_2$ are described before.

When $R_1$ and $R_2$ are methyl, said compound of formula VII refers to the 7-methoxycarbonyl-9-(methoxycarbonylmethyl)-3-[(tetrahydro-2H-pyran2-yl)oxy]-9-azabicyclo [3.3.1]nonane (referred to as PAN) of the following formula.

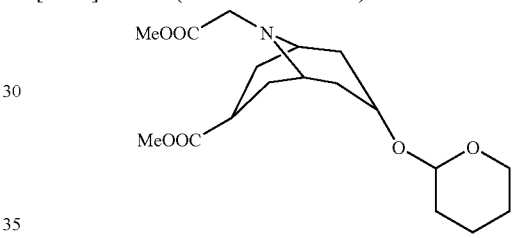

Figure 7:
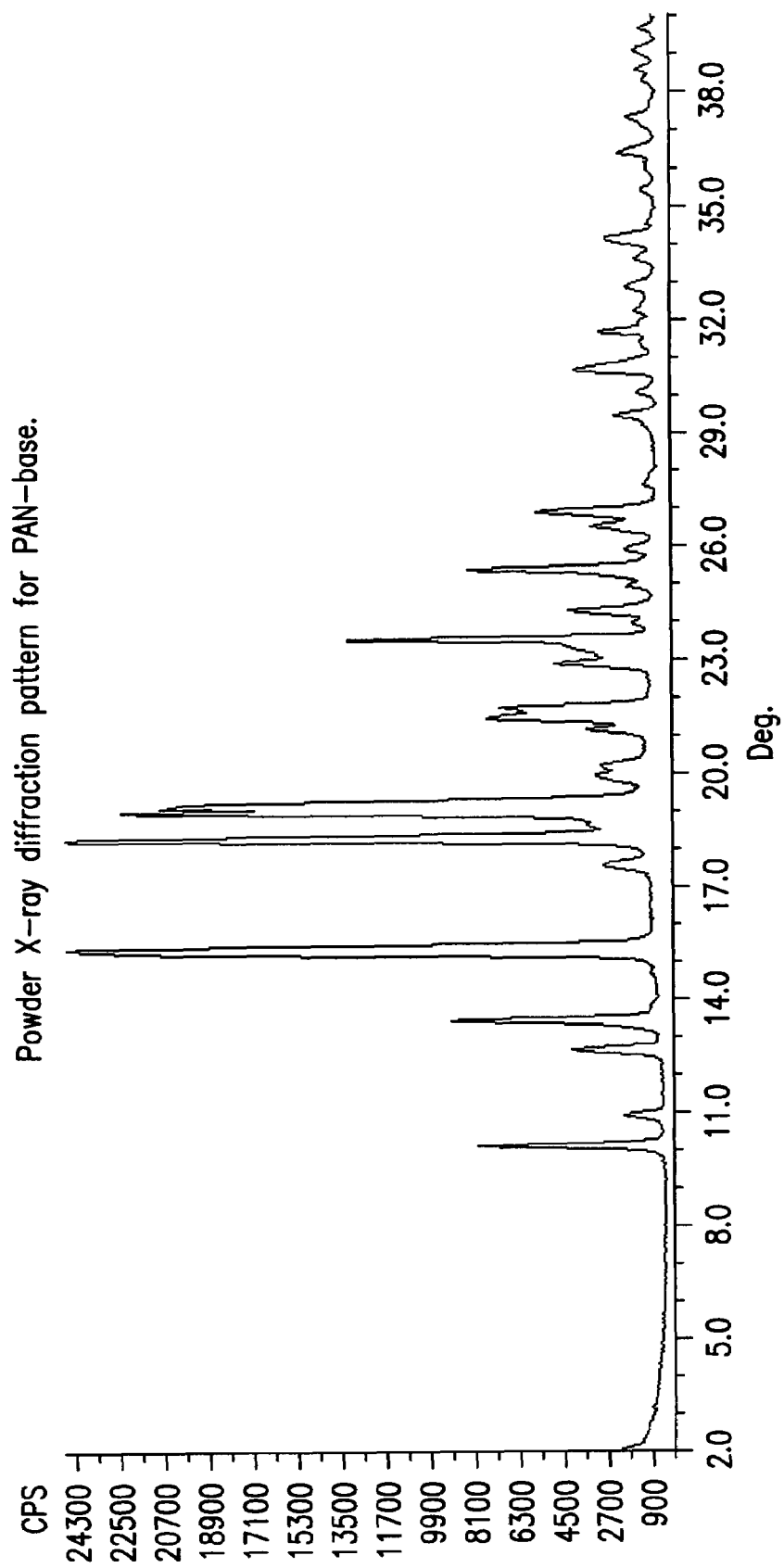
FIG. 7 illustrates powder X-ray diffraction pattern for PAN-base.
Figure 8:
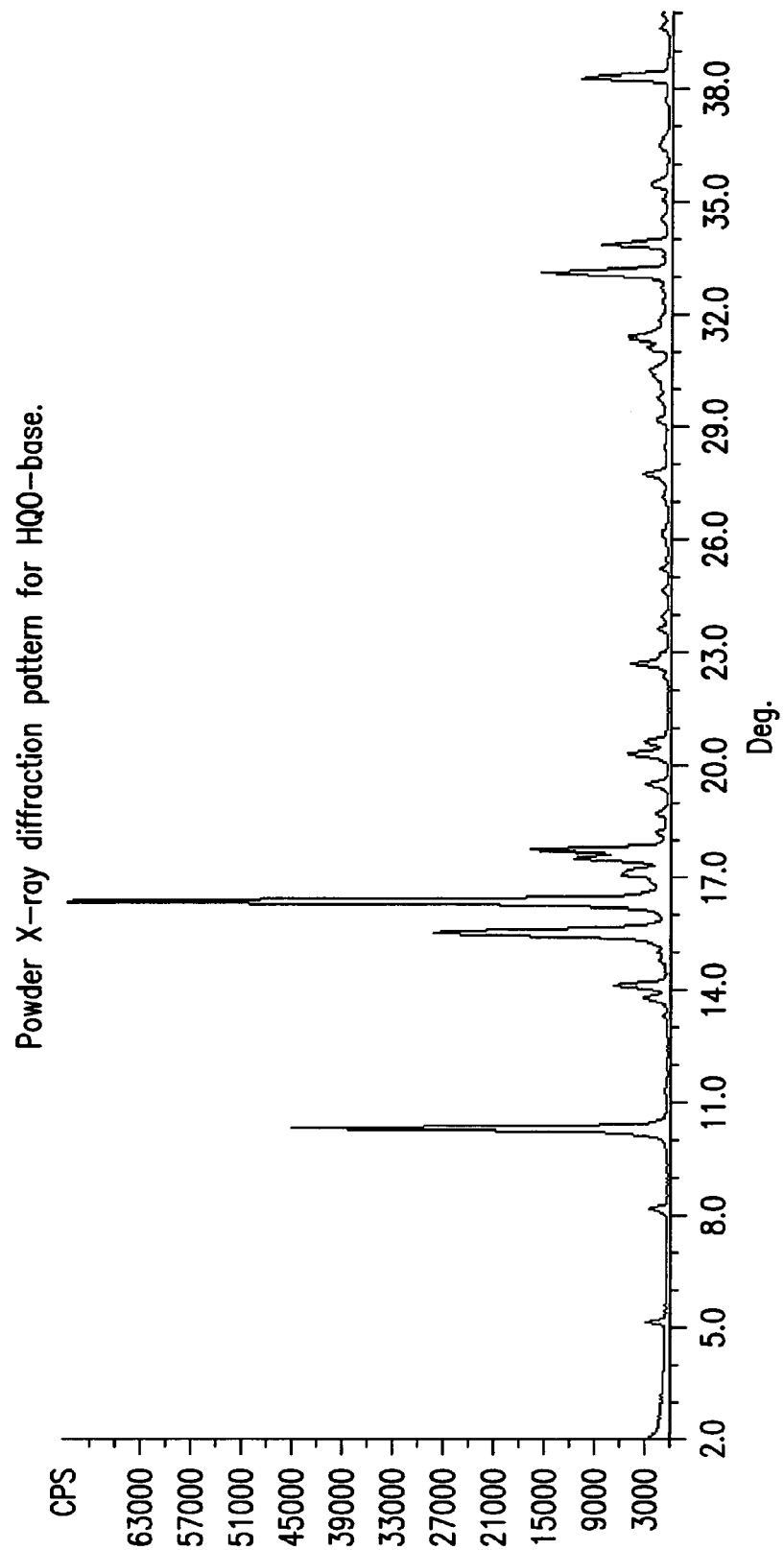
FIG. 8 illustrates powder X-ray diffraction pattern for HQO-base.

The present invention also provides crystalline PAN. The crystalline PAN of the present invention may be characterized by a powder XRD diffraction pattern having peaks at about 10.1, 15.3, and 18.2 degrees two-theta, ±0.2 degrees two-theta. The crystalline PAN may be further characterized by a powder XRD diffraction having peaks at about 10.1, 12.6, 13.4, 15.3, 18.2, 18.9, 19.2, 23.5, and 25.4 degrees two-theta, ±0.2 degrees two-theta. The crystalline PAN may be also substantially identified by the PXRD pattern as depicted in FIG. 7.

The present invention provides a quaternary ammonium salt of a 7-alkoxycarbonyl-9-(alkoxycarbonylmethyl)-3-[(tetrahydro-2H-pyran2-yl)oxy]-9-azabicyclo[3.3.1]nonane compound (referred to as a PAN-salt) of formula VIIs;

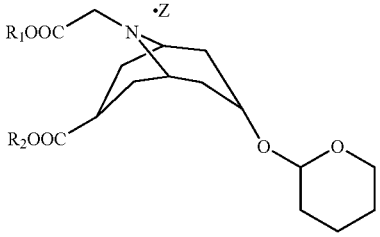

VIIs wherein $R_1$, $R_2$ and Z are described before.

When $R_1$ and $R_2$ are methyl and Z is methanesulfonic acid, said compound of formula VIIs refers to the methanesulfonate salt of 7-methoxycarbonyl-9-(methoxycarbonylmethyl)-3-[(tetrahydro-2H-pyran2-yl)oxy]-9-azabicyclo [3.3.1]nonane (referred to as PAN-MsOH) of the following formula.

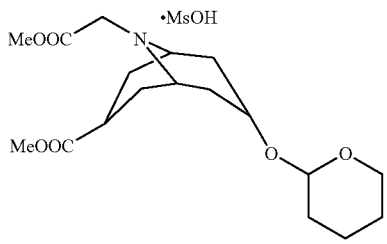

Figure 1:
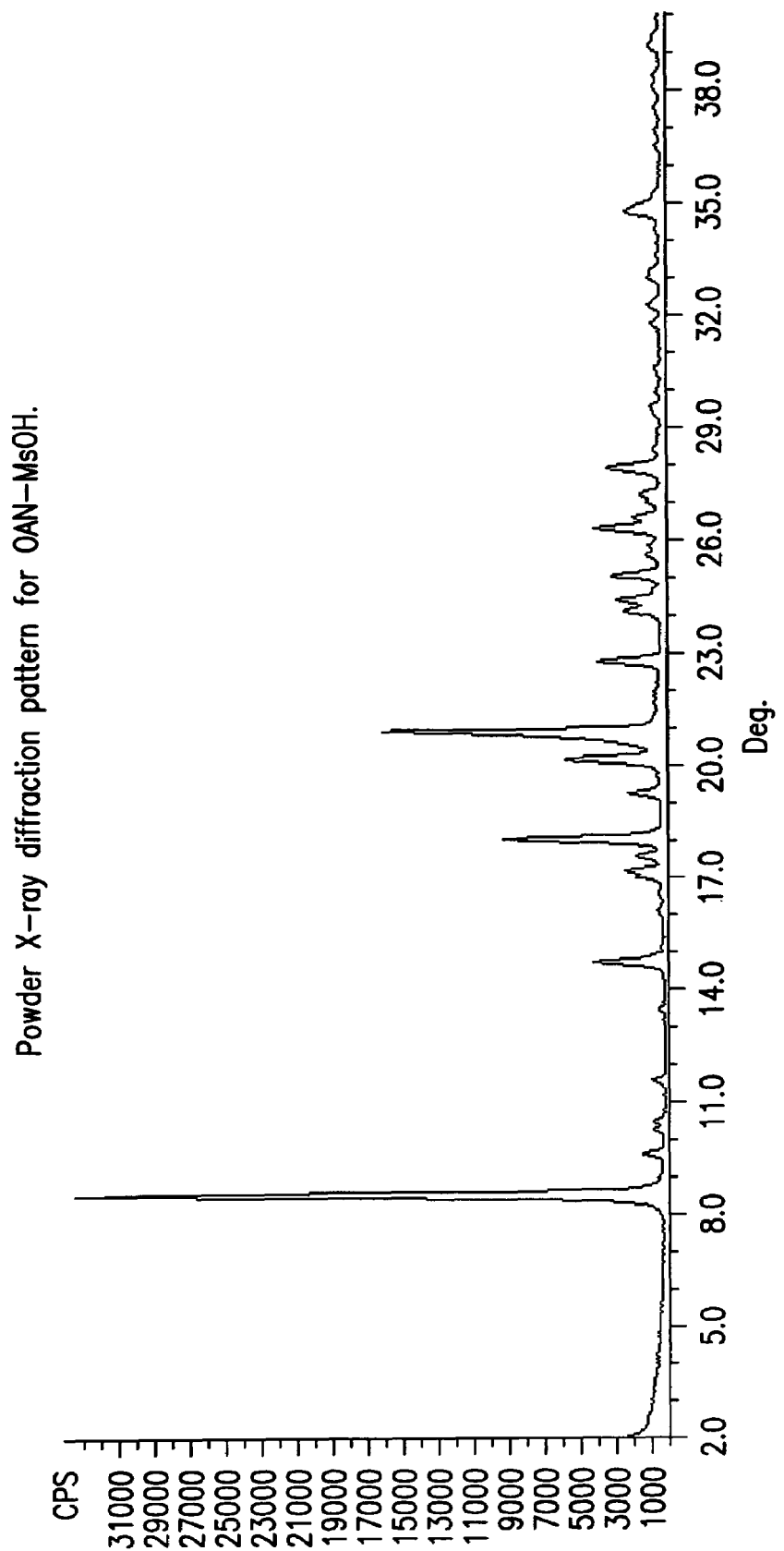
FIG. 1 illustrates powder X-ray diffraction pattern for OAN-MsOH.
Figure 2:
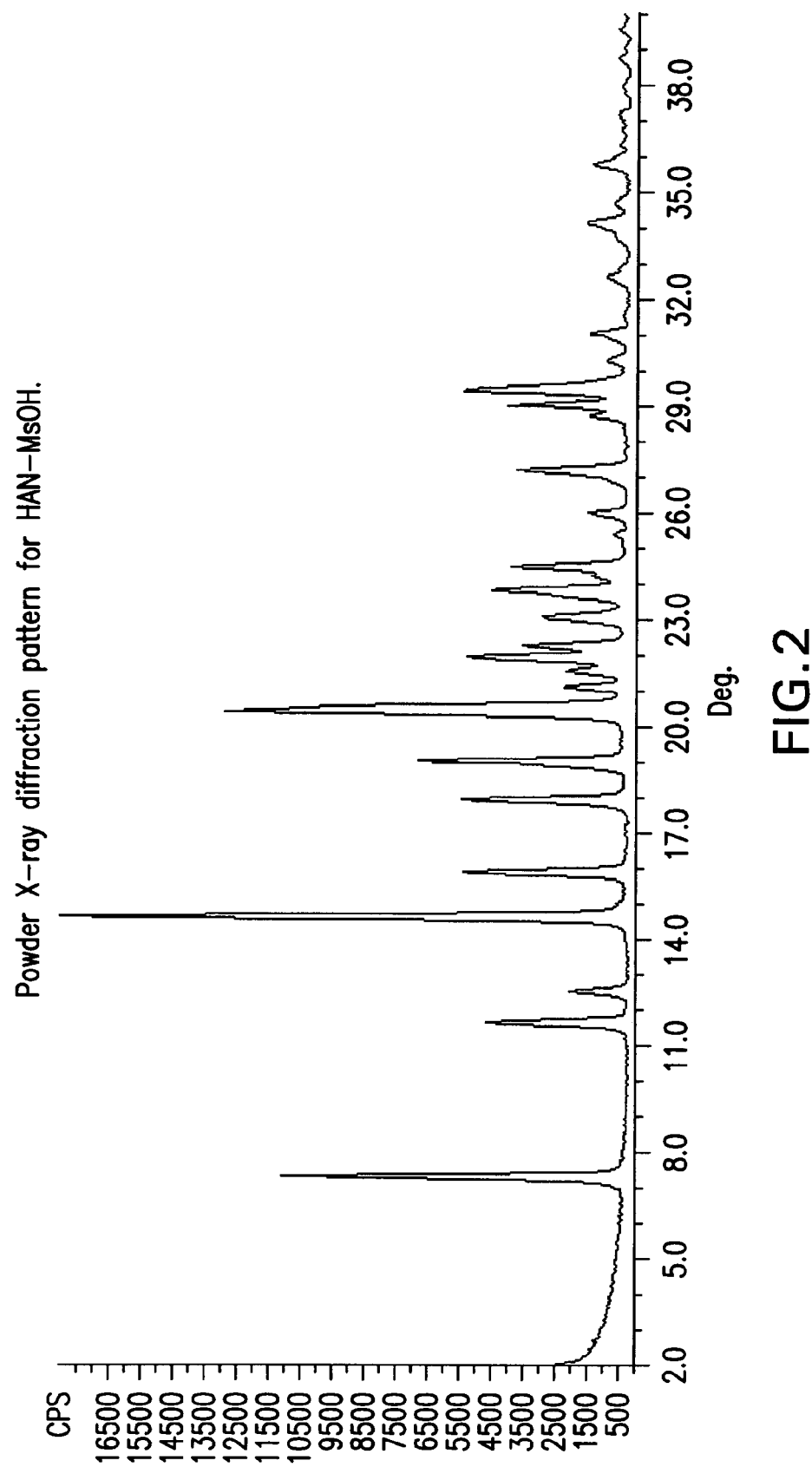
FIG. 2 illustrates powder X-ray diffraction pattern for HAN-MsOH.
Figure 3:
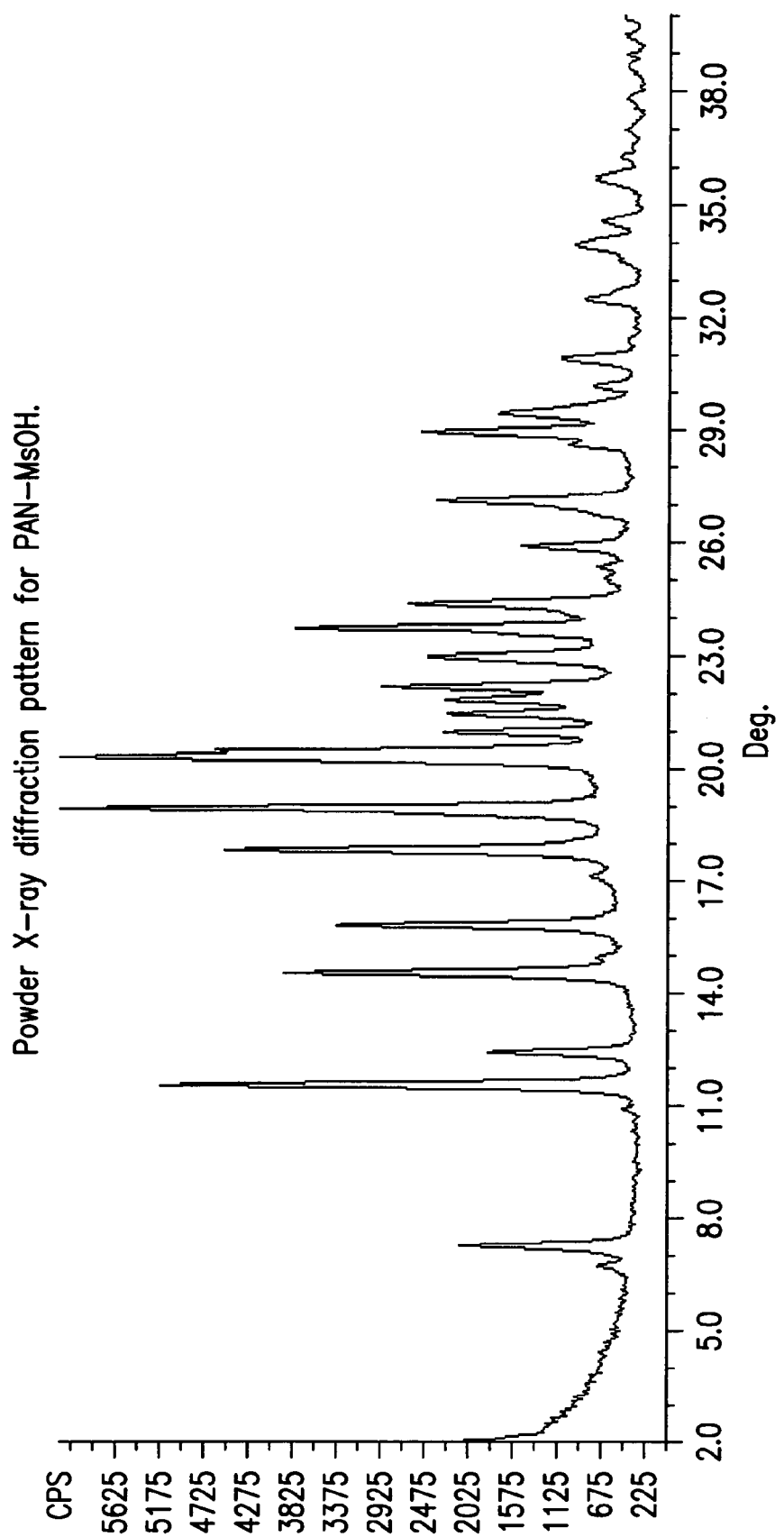
FIG. 3 illustrates powder X-ray diffraction pattern for PAN-MsOH.
Figure 4:
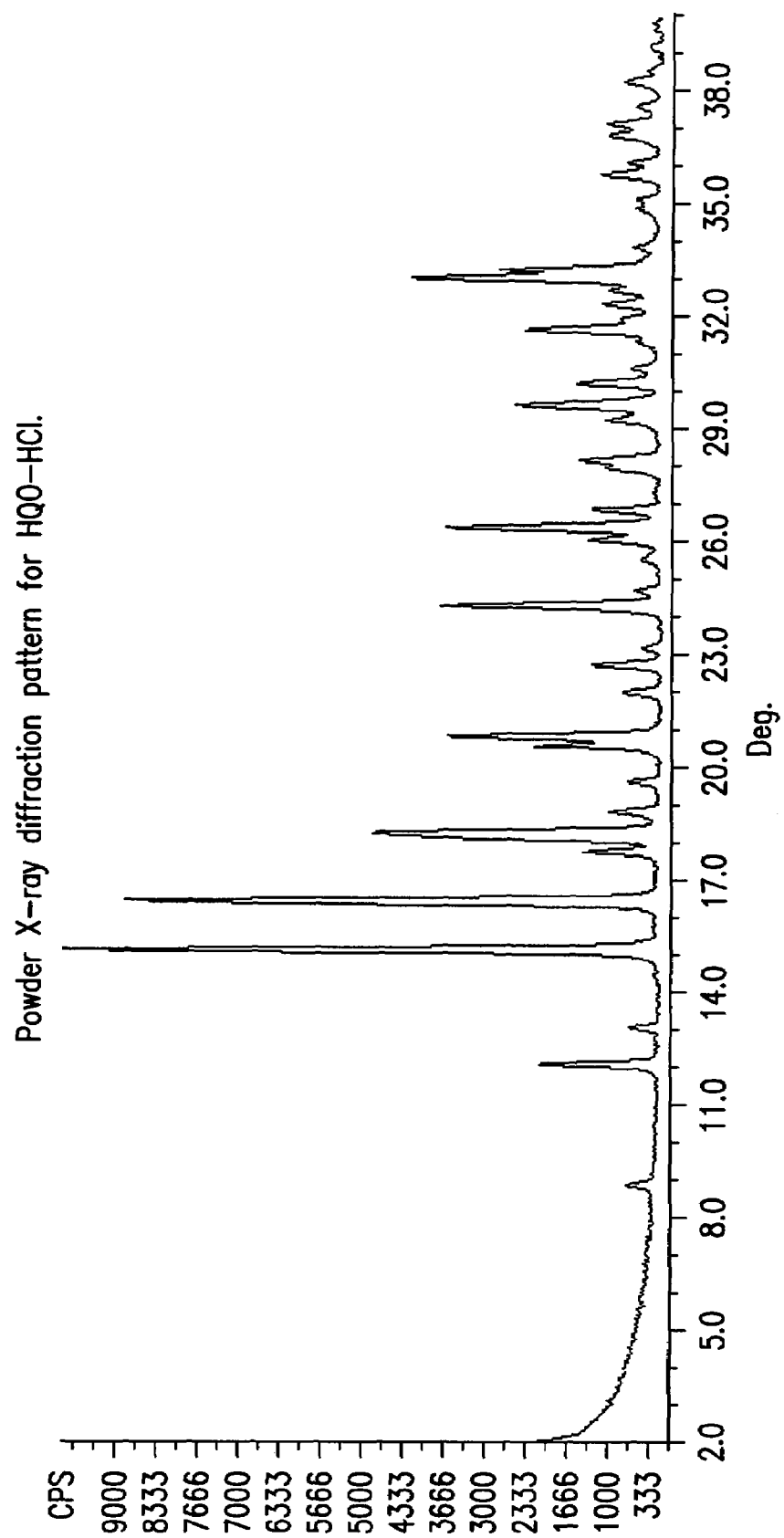
FIG. 4 illustrates powder X-ray diffraction pattern for HQO-HCl.

The present invention further provides crystalline PAN-MsOH. The crystalline PAN-MsOH of the present invention may be characterized by a powder XRD diffraction pattern having peaks at about 7.3, 11.6, and 14.6 degrees two-theta, ±0.2 degrees two-theta. The crystalline PAN-MsOH may be further characterized by a powder XRD diffraction pattern having peaks at about 6.7, 12.5, 15.9, 17.1, 17.9, 19.0, 20.4, 22.2, and 23.8 degrees two-theta, ±0.2 degrees two-theta. The crystalline PAN-MsOH may also be substantially identified by the PXRD pattern as depicted in FIG. 3.

The present invention also provides an isolated endo-9-alkoxycarbonyl-5-[(tetrahydro-2H-pyran-2-yl)oxy]-8-azatricyclo[5.3.1.0$^{3,8}$]undecan-10-one (trans-hexahydro-4-alkoxycarbonyl-8-[(tetrahydro-2H-pyran-2-yl)oxy]-2,6-methano-2H-quinolizin-3(4H)-one) compound (referred to as a PQO compound) of formula IX,

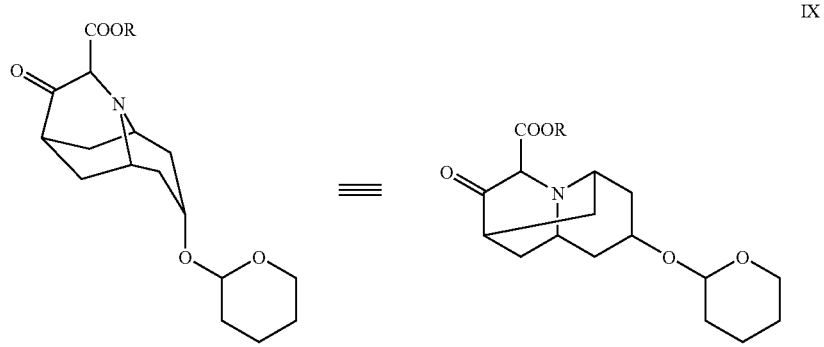

wherein R is a $C_{1-6}$ alkyl or a $C_{6-8}$ aryl, preferably, a $C_{1-4}$ alkyl, more preferably, methyl.

When R is methyl, said compound of formula IX refers to endo-9-methoxycarbonyl-5-[(tetrahydro-2H-pyran-2-yl)oxy]-8-azatricyclo[5.3.1.0$^{3,8}$]undecan-10-one (trans-hexahydro-4-methoxycarbonyl-8-[(tetrahydro-2H-pyran-2-yl)oxy]-2,6-methano-2H-quinolizin-3(4H)-one) (referred to as PQO) of the following formula.

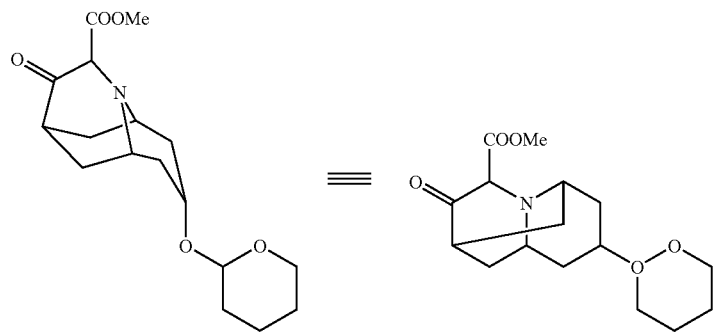

Figure 5:
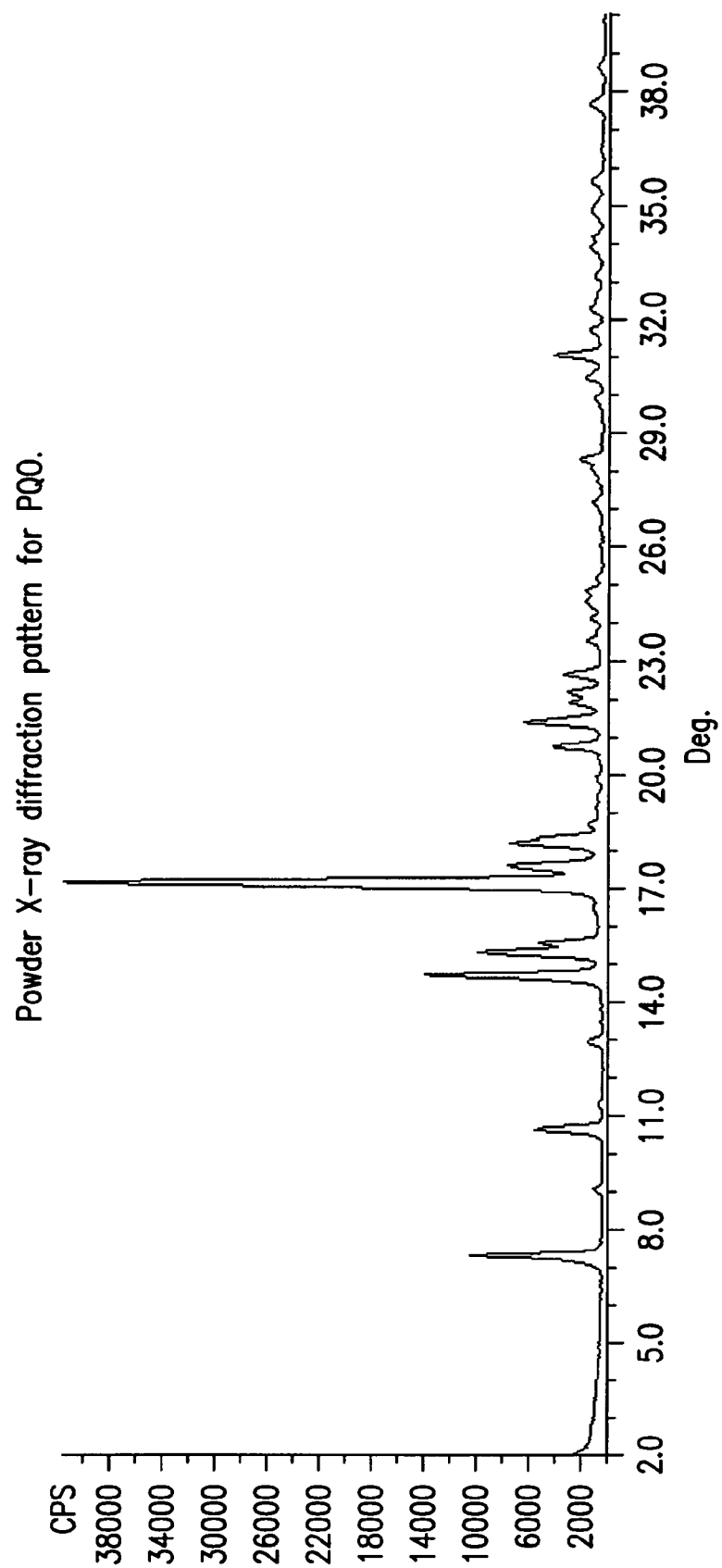
FIG. 5 illustrates powder X-ray diffraction pattern for PQO.
Figure 6:
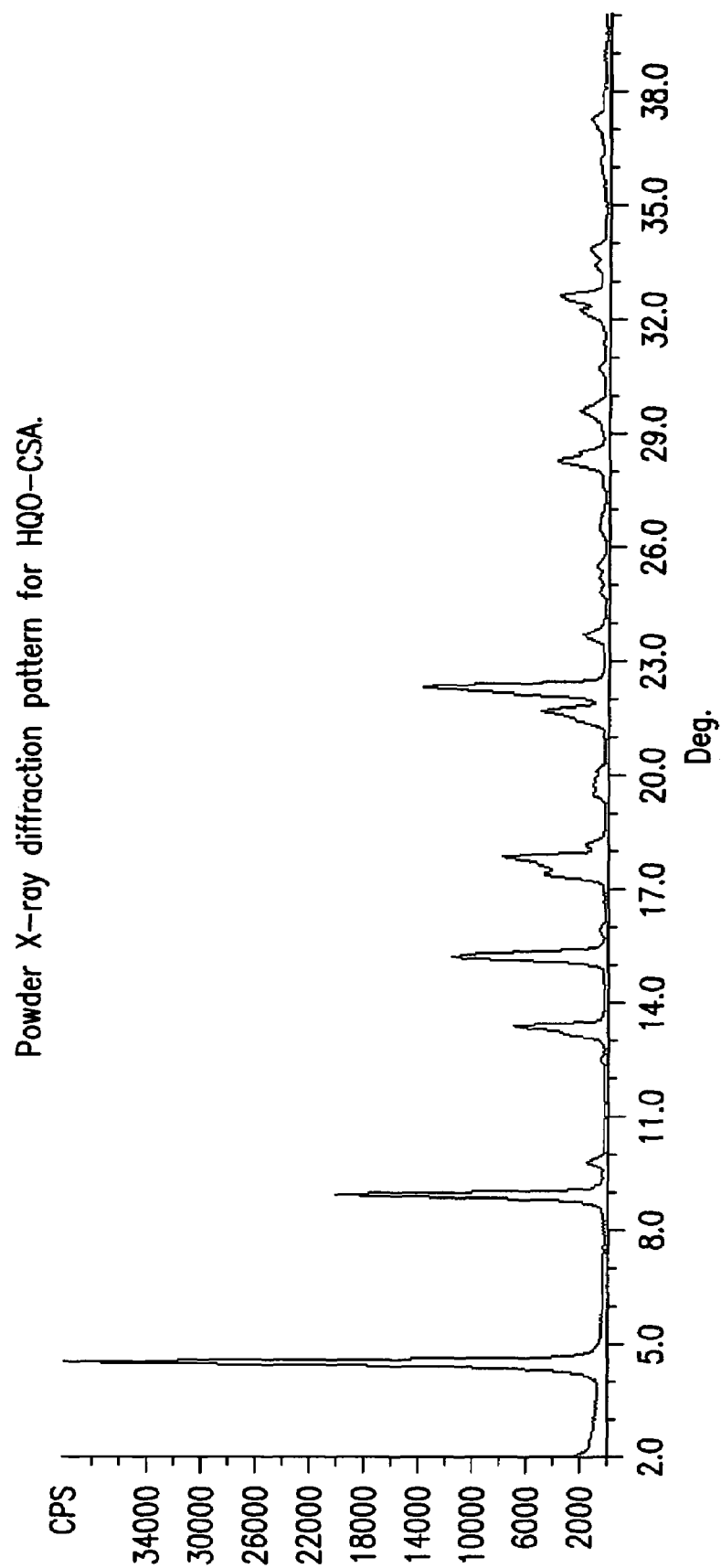
FIG. 6 illustrates powder X-ray diffraction pattern for HQO-CSA.

The present invention provides crystalline PQO. The crystalline PQO of the present invention may be characterized by a powder XRD diffraction pattern having peaks at about 7.3, 14.7, and 17.2 degrees two-theta, ±0.2 degrees two-theta. The crystalline PQO may be further characterized by a powder XRD diffraction pattern having peaks at about 10.7, 15.3, 17.6, 18.2, and 21.4 degrees two-theta, ±0.2 degrees two-theta. The crystalline PQO may also be substantially identified by the PXRD pattern as depicted in FIG. 5.

The present invention provides a 7-alkoxycarbonyl-9-(alkoxycarbonylmethyl)-3-acyloxy-9-azabicyclo[3.3.1]nonane compound (referred to as a PivAN compound) of formula XIII;

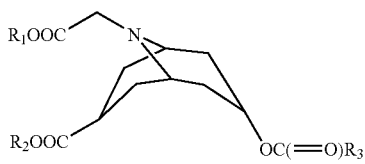

XIII wherein $R_1$ and $R_2$ are independently a $C_{1-6}$ alkyl or a $C_{6-8}$ aryl, preferably, a $C_{1-4}$ alkyl, more preferably, methyl, and $R_3$ is a $C_{1-6}$ alkyl or a $C_{6-8}$ aryl, preferably, a $C_{1-4}$ alkyl, more preferably, tert-butyl.

When $R_1$ and $R_2$ are methyl, and $R_3$ is tert-butyl, said compound of formula XIII refers to 7-methoxycarbonyl-9-(methoxycarbonylmethyl)-3-pivaloyloxy-9-azabicyclo[3.3.1]nonane (referred to as PivAN) of the following formula.

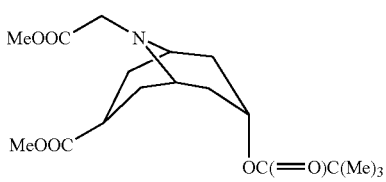

In the present invention a process for the preparation of a CCA-epoxide of formula IV

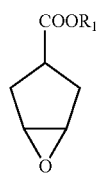

IV may comprise combining a CCA-ester of formula III,

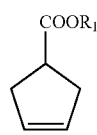

III an oxidizing agent selected from the group consisting of: a hydroperoxide, a dialkyl peroxide, a peroxyacid, a peroxyester, a diacyl peroxide, a persulphate, a perborate, a perphosphate, and a dimethyldioxiran, a catalyst, and a solvent selected from the group consisting of water, water miscible organic solvents, and mixtures thereof, forming a reaction mixture to obtain the CCA-epoxide of formula IV, wherein $R_1$ is a $C_{1-6}$ alkyl or a $C_{6-8}$ aryl, preferably, a $C_{1-4}$ alkyl, more preferably, methyl.

When $R_1$ is methyl, said CCA-ester of formula III corresponds to CCA-methylester of the following formula,

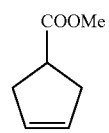

and said CCA-epoxide of formula IV corresponds to CCA-epoxide of the following formula.

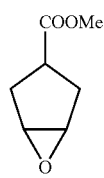

Preferably, the CCA-ester of formula III is combined with a solvent selected from the group consisting of water, water miscible organic solvents, and mixtures thereof, to obtain a solution.

Preferably, the water miscible organic solvent is selected from the group consisting of linear or branched $C_{1-4}$ alcohols. Preferably, the $C_{1-4}$ alcohol is a $C_{1-3}$ alcohol, more preferably, a $C_{1-2}$ alcohol, most preferably, methanol. In the alternative, a mixture of water and a water immiscible organic solvent may be used in the presence of a phase transfer catalyst. Preferably, the water immiscible organic solvent is selected from the group consisting of a $C_{1-8}$ halogenated hydrocarbon, a $C_{2-8}$ ester, a $C_{2-8}$ ether and a $C_{3-6}$ ketone. A preferred $C_{1-8}$ halogenated hydrocarbon is a $C_{1-4}$ halogenated hydrocarbon, more preferably a $C_{1-2}$ halogenated hydrocarbon. Preferably, the $C_{1-2}$ halogenated hydrocarbon is dichloromethane, 1,2-dichloroethane or chloroform, more preferably dichloromethane. A preferred $C_{2-8}$ ester is a $C_{2-6}$ ester, more preferably, a $C_{4-6}$ ester. Preferably, the $C_{4-6}$ ester is ethyl acetate, n-butyl acetate or isobutyl acetate, more preferably ethyl acetate. A preferred $C_{2-8}$ ether is a $C_{2-6}$ ether, more preferably, a $C_{4-6}$ ether. Preferably, the $C_{4-6}$ ether is diethyl ether, diisopropyl ether or tert-butyl methyl ether, more preferably tert-butyl methyl ether. A preferred $C_{3-6}$ ketone is a $C_{4-6}$ ketone. Preferably, the $C_{4-6}$ ketone is methyl ethyl ketone (2-butanone), 2-pentanone, 3-pentanone or 3,3-dimethyl-2-butanone, more preferably 2-pentanone. The most preferred solvent is dichloromethane. Further, the phase transfer catalyst is preferably a quaternary ammonium salt, more preferably the phase transfer catalyst is tetrabutyl ammonium bromide.

Preferably, the solution is combined with an oxidizing agent selected from the group consisting of: a hydroperoxide, a dialkyl peroxide, a peroxyacid, a peroxyester, a diacyl peroxide, a persulphate, a perborate, a perphosphate, and a dimethyldioxiran, and a catalyst, to obtain a mixture.

Preferably, the hydroperoxide is RO—OH, wherein R is either H or an alkyl group. Preferably, the alkyl group is a $C_{1-6}$ alkyl, more preferably t-butyl. A preferred dialkyl peroxide is RO—OR, wherein R is a $C_{1-6}$ alkyl, preferably t-butyl. Preferably, the peroxyacid is RCO—O—OH. More preferably, the RCO—O—OH is selected from the group consisting of: peracetic acid, trifluoroperacetic acid, perlauric acid, perbenzoic acid, and 3,5-dinitroperbenzoic acid. Preferably, the peroxyester is RCO—O—OR', wherein R is phenyl or methyl, and R' is an $C_{1-6}$ alkyl, preferably t-butyl. A preferred diacyl peroxide is RCO—O—O—COR, wherein R is phenyl or methyl. A preferred persulphate is peroxydisulphuric acid ($M_2S_2O_8$) in the form of a potassium, sodium or ammonium (M=K, Na, $NH_4$) salt, peroxymonosulfuric acid (Caro's acid), and Oxone® (potassium monopersulfate triple salt: $KHSO_5$—$KHSO_4$—$K_2SO_4$ (2:1:1)"). The more preferred oxidizing agent is hydroperoxide, most preferably, hydrogen peroxide. Preferably, an aqueous solution of hydrogen peroxide is used. A preferred concentration of the solution is of about 3% to about 50%, more preferably of about 20% to about 40%, most preferably of about 30% to about 35%.

Preferably, the catalyst is selected from the group consisting of Zeolites and polyoxometalates. Preferably, the metal moiety of the polyoxometalates is selected from the group consisting of tungsten, molybdenum, rhenium, vanadium and niobium. More preferably, the catalyst is either sodium tungstate dihydrate or sodium molybdenate dihydrate.

A preferred amount of the catalyst is about 0.01 mole % to about 50 mole % per mole of the CCA-ester, more preferably about 1 mole % to about 10 mole % per mole of the CCA-ester, most preferably about 2 mole % per mole of the CCA-ester.

In preparing the CCA epoxide of formula IV, the reaction mixture is maintained at a temperature of about 0° C. to about 80° C., preferably about 30° C. to about 80° C., more preferably, at a temperature of about 15° C. to about 65° C., most preferably at a temperature of about 60° C. to about 65° C. The reaction mixture is preferably, maintained at such temperature for a period of about 0.5 hours to about 24 hours, more preferably for about 1 to about 10 hours, most preferably for about 2 hours to about 4 hours.

The progress of the reaction may be monitored by gas-chromatography (referred to as GC) or by thin-layer chromatography (referred to as TLC). When monitored by TLC, an eluent of n-hexane and ethylacetate in a ratio of 1:1 may be used.

The process for preparing a CCA-ester of formula IV may further comprise a recovery step. The CCA-epoxide of formula IV may be recovered comprising the steps of adjusting the temperature of the reaction mixture to a temperature of about 20° C. to about 30° C.; extracting the product with a water immiscible organic solvent, preferably, dichloromethane; and evaporating the solvent.

The process for preparing a CCA-ester of formula IV may further comprise a process for converting it to a DLS-salt of formula VIIIs,

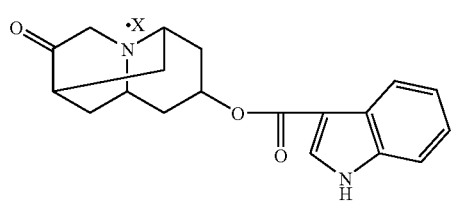

VIIIs wherein, X is an acid selected from the group consisting of: hydrochloric acid, hydrobromic acid, sulfuric acid, nitric acid, phosphoric acid, perchloric acid, fluoroboric acid, formic acid, acetic acid, propionic acid, trichloroacetic acetic, trifluoroacetic acid, maleic acid, fumaric acid, succinic acid, oxalic acid, tartaric acid, citric acid, mandelic acid, benzoic acid, salicylic acid, naphthalene carboxylic and dicarboxylic acids, methanesulfonic acid, ethanesulfonic acid, trifluoromethanesulfonic acid, p-toluenesulfonic acid, camphorsulfonic acid, benzenesulfonic acid, naphthalene sulfonic and disulfonic acids, preferably, methane sulfonic acid. This conversion to a DLS salt of formula VIIIs may be carried out by the process of the invention or any other known process converting the CCA epoxide of formula IV to a DLS salt of formula VIIIs as described for example in EP 0339699, example 9.

When X is methane sulfonic acid, said DLS-salt of formula VIIIs corresponds to DLS-MsOH of the following formula.

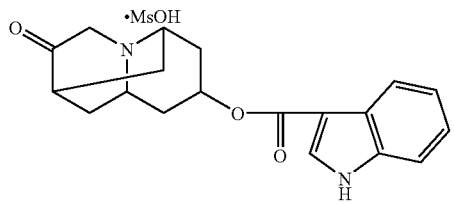

The process of the present invention provides an OAN compound of formula V prepared by a process comprising an oxidation reaction followed by Robinson-Schöpf reaction, wherein both reactions are done in water, and therefore can be done concurrently, i.e., without isolation of the oxidation product, prior to the Robinson-Schöpf reaction. The oxidation applies the use of periodic acid in water, in which the reagents and the reduction products have high solubility; hence, the reaction is fast. Also, using water allows controlling the exothermic nature of the reaction, thus, reducing the danger.

The present invention further provides a process for the preparation of an OAN compound of formula V

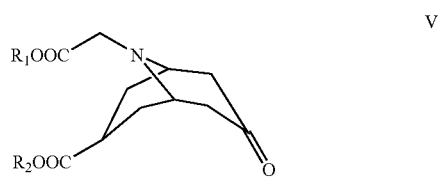

V comprising combining a) a CCA-epoxide of formula IV, an oxidizing agent, and a solvent selected from the group consisting of water, water miscible organic solvents, and mixtures thereof, to form a reaction mixture; b) raising the pH of the reaction mixture; c) adding to the reaction mixture of step b) a pH 4 buffer, glycine $C_{1-4}$ ester or salts thereof, and a substance comprising carbonyl moiety selected from the group consisting of 1,3-acetonedicarboxylic acid, acetone and a $C_{1-4}$ ester thereof, to form the OAN compound of formula V, wherein $R_1$ and $R_2$ are independently a $C_{1-6}$ alkyl or a $C_{6-8}$ aryl, preferably, a $C_{1-4}$ alkyl, more preferably, methyl.

When $R_1$ and $R_2$ are methyl, said OAN compound of formula V corresponds to OAN of the following formula.

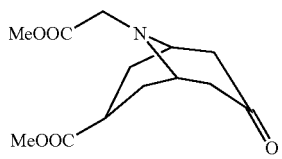

Combining a CCA-epoxide of formula IV, an oxidizing agent, and a solvent selected from the group consisting of water, water miscible organic solvents, and mixtures thereof, to form a reaction mixture; and raising the pH of the reaction mixture, may be designated as an oxidation reaction.

Preferably, combining a CCA-epoxide of formula IV with an oxidizing agent, and a solvent selected from the group consisting of water, water miscible organic solvent and mixtures thereof provides a first reaction mixture.

Preferably, the water miscible organic solvent is selected from the group consisting of: a nitrile, a ketone and an ether. A preferred nitrile is a $C_{2-4}$ nitrile. Preferably, the $C_{2-4}$ nitrile is acetonitrile, propionitrile or butyronitrile. A preferred ketone is a $C_{3-6}$ ketone. Preferably, the $C_{3-6}$ ketone is acetone, methyl ethyl ketone or diethyl ketone. Preferably, the ether is a cyclic ether. A preferred cyclic ether is THF, 1,4-dioxane or 1,3-dioxolane. The preferred solvent is water.

Preferably, the oxidizing agent is selected from the group consisting of: periodic acid and salts thereof, lead tetraacetate, cerium and ammonium nitrate $(Ce(NH_4)_2(NO_3)_6)$. More preferably, the oxidizing agent is periodic acid. Preferably, the oxidizing agent is added in the form of a solution when the solvent is water.

Preferably, the first reaction mixture is maintained at a temperature of about 10° C. to about 60° C., more preferably at a temperature of about 10° C. to about 15° C. Preferably, the first mixture is maintained for a period of about 0.5 hours to about 24 hours, and more preferably for about 1 to about 3 hours. Maintaining the first reaction mixture is preferably done while stirring.

The first reaction mixture is, preferably, acidic. Preferably, the pH of the acidic first reaction mixture is of about 0.5 to about 7, more preferably of about 0.5 to about 2.

Preferably, the pH of the maintained first reaction mixture is increased to about 2 to about 7. The pH is raised, preferably to about 3.5 to about 4.5. Preferably, the pH is raised by using a water immiscible base, more preferably either poly(4-vinylpyridine) or OH resins, and even more preferably, OH resins. The water immiscible base is, preferably, filtered off, more preferably through Celite, providing an aqueous solution of the product of the oxidation reaction. Preferably, adjusting the pH is performed at a temperature of about 15° C. to about 35° C., more preferably at about room temperature.

The reaction may be run stepwise or concurrently, i.e., without isolation of the oxidation product prior to the Robinson-Schöpf reaction. Preferably, the process is run concurrently.

Preferably, after adjusting the pH, a pH 4 buffer, a glycine $C_{1-4}$ ester or salts thereof, and a substance comprising carbonyl moiety selected from the group consisting of a 1,3-acetonedicarboxylic acids, acetone and $C_{1-4}$ esters thereof, are added to obtain a second reaction mixture.

Preferably, the pH 4 buffer is an amine-free buffer. Preferably, the amine-free buffer is selected from the group consisting of: a citric acid-sodium hydroxide-hydrochloric acid buffer, a citric acid-disodium hydrogenphosphate buffer, a sodium acetate-acetic acid buffer, a potassium diphthalate-sodium hydroxide buffer, sodium dihydrogen phosphate and potassium hydrogen phthalate. More preferably, the amine-free buffer is potassium hydrogen phthalate. Preferably, the buffer is used in an amount of about 1 to about 10 mole equivalents, more preferably about 2 to 5 mole equivalents, most preferably about 3 mole equivalents, per mole equivalent of the CCA-epoxide.

Preferably, the glycine $C_{1-4}$ ester is a methyl ester. A preferred salt of the glycine $C_{1-4}$ ester is glycine hydrochloride. More preferably, the glycine $C_{1-4}$ ester or salts thereof, is glycin methylester hydrochloride.

Preferably, the $C_{1-4}$ ester of 1,3-acetonedicarboxylic acid is selected from the group consisting of symmetrical and mixed $C_{1-4}$ ester derivatives. The preferred substance comprising a carbonyl moiety is 1,3-acetonedicarboxylic acid.

Preferably, the second reaction mixture is maintained at a temperature of about 0° C. to about 60° C., more preferably, at about 10° C. to about 40° C., most preferably at about room temperature. The second mixture is maintained, preferably for about 10 to about 72 hours, and more preferably for about 12 to about 24 hours, most preferably for about 18 hours. Maintaining the second reaction mixture is preferably done while stirring.

The process for preparing the OAN compound of formula V may further comprise a recovery step. The recovery may be done by any known process. The OAN compound of formula V may be recovered by filtering off the undissolved solid particles from the second reaction mixture, preferably, through Celite, followed by washing with water, and combining the filtrate with an inorganic base to obtain a pH of about 7 to about 9, more preferably, of about 7.5 to about 8. Preferably, the inorganic base is selected from the group consisting of sodium hydroxide, sodium carbonate, sodium bicarbonate, potassium hydroxide, potassium carbonate and potassium bicarbonate, more preferably is sodium bicarbonate. The basic filtrate is then extracted with a water immiscible organic solvent, preferably a $C_{2-5}$ acetate, more preferably isobutylacetate, and the solvent is evaporated.

The present invention also provides a process for the preparation of a DLS-salt of formula VIIIs comprising preparing the OAN compound of formula V by the process of the invention, and converting it to a DLS-salt of formula VIIIs. This conversion to a DLS salt of formula VIIIs may be carried out by the process of the invention or any other known process converting an OAN compound of formula V to a DLS salt of formula VIIIs as described for example in EP 0339699, examples 4 and 9.

The present invention provides a process for the preparation of an OAN-salt of formula Vs

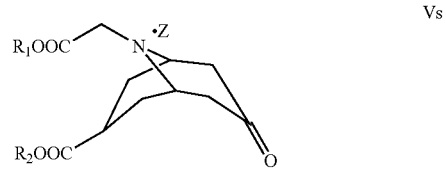

comprising reacting the OAN compound of formula V, an acid, and an organic solvent selected from the group consisting of a $C_{1-4}$ alcohol, a $C_{2-8}$ ester, a linear, branched or cyclic $C_{2-8}$ ether, a $C_{3-6}$ ketone and a $C_{5-8}$ aliphatic hydrocarbon, a $C_{1-8}$ halogenated hydrocarbon, a $C_{1-4}$ nitroalkane, a $C_{1-4}$ alkylcyanide, a $C_{6-8}$ aromatic hydrocarbon, a $C_{3-10}$ amide and mixtures thereof, wherein, $R_1$ and $R_2$ are described before, and Z is an acid, preferably, methanesulfonic acid.

The present invention further provides a process for purifying the OAN compound of formula V comprising reacting the OAN compound of formula V, an acid, and an organic solvent selected from the group consisting of a $C_{1-4}$ alcohol, a $C_{2-8}$ ester, a linear, branched or cyclic $C_{2-8}$ ether, a $C_{3-6}$ ketone and a $C_{5-8}$ aliphatic hydrocarbon, a $C_{1-8}$ halogenated hydrocarbon, a $C_{1-4}$ nitroalkane, a $C_{1-4}$ alkylcyanide, a $C_{6-8}$ aromatic hydrocarbon, a $C_{3-10}$ amide and mixtures thereof; and adding a base.

The OAN compound of formula V used as a starting material may be a crude OAN compound or a concentrated solution of a crude OAN compound, obtained in the recovery process of the OAN compound.

Preferably, the OAN compound of formula V is dissolved in an organic solvent selected from the group consisting of a $C_{1-4}$ alcohol, a $C_{2-8}$ ester, a linear, branched or cyclic $C_{2-8}$ ether, a $C_{3-6}$ ketone and a $C_{5-8}$ aliphatic hydrocarbon, a $C_{1-8}$ halogenated hydrocarbon, a $C_{1-4}$ nitroalkane, a $C_{1-4}$ alkylcyanide, a $C_{6-8}$ aromatic hydrocarbon, a $C_{3-10}$ amide and mixtures thereof, prior to adding the acid.

Preferably, the $C_{1-4}$ alcohol is a $C_{1-3}$ alcohol. Preferably, the $C_{1-3}$ alcohol is methanol, n-propanol, isopropanol or ethanol. A preferred $C_{2-8}$ ester is a $C_{2-6}$ ester, more preferably, a $C_{2-4}$ ester. A preferred $C_{2-4}$ ester is ethyl acetate, propylacetate, n-butyl acetate, or isobutylacetate. A preferred linear, branched or cyclic $C_{2-8}$ ether is a $C_{2-7}$ ether, more preferably, a $C_{2-5}$ ether. A preferred $C_{2-5}$ ether is 1,4-dioxane, diisopropyl ether, t-butyl methyl ether or tetrahydrofuran. Preferably, the $C_{3-6}$ ketone is a $C_{3-5}$ ketone. Preferably, the $C_{3-5}$ ketone is methyl ethyl ketone (2-butanone), 2-pentanone, 3-pentanone, 3,3-dimethyl-2-butanone or acetone. Preferably, the $C_{5-8}$ aliphatic hydrocarbon is a $C_{5-7}$ aliphatic hydrocarbon, more preferably, a $C_{6-7}$ aliphatic hydrocarbon. A preferred $C_{6-7}$ aliphatic hydrocarbon is either n-hexane, or n-heptane. A preferred $C_{1-8}$ halogenated hydrocarbon is a $C_{1-6}$ halogenated hydrocarbon, more preferably a $C_{1-4}$ halogenated hydrocarbon, most preferably a $C_{1-2}$ halogenated hydrocarbon. A preferred $C_{1-2}$ halogenated hydrocarbon is dichloroethane, chloroform or dichloromethane. A preferred $C_{1-4}$ nitroalkane is a $C_{1-2}$ nitroalkane. Preferably, the $C_{1-2}$ nitroalkane is nitromethane or nitroethane. Preferably, the $C_{1-4}$ alkylcyanide is a $C_{1-3}$ alkylcyanide. A preferred $C_{1-3}$ alkylcyanide is either propionitrile or acetonitrile. A preferred $C_{6-8}$ aromatic hydrocarbon is a $C_{6-7}$ aromatic hydrocarbon. Preferably, the $C_{6-7}$ aromatic hydrocarbon is toluene. A preferred $C_{3-10}$ amide is a $C_{3-6}$ anide. Preferably, the $C_{3-6}$ amide is dimethylformamide. The more preferred solvent is a mixture of a $C_{2-4}$ ester and a $C_{1-3}$ alcohol, more preferably, of isobutylacetate and ethanol. Preferably, the mixture contains isobutylacetate and ethanol in a ratio of about 1:1, respectively.

Preferably, the acid is either an organic acid or an inorganic acid. The organic acid is selected from the group consisting of carboxylic acids and sulfonic acids. Preferably, the carboxylic acid is selected from the group consisting of: formic acid, acetic acid, propionic acid, trichloroacetic acetic, trifluoroacetic acid, maleic acid, fumaric acid, succinic acid, oxalic acid, tartaric acid, citric acid, mandelic acid, benzoic acid, salicylic acid, naphthalene carboxylic and dicarboxylic acids. More preferably, the carboxylic acid is tartaric acid. A preferred sulfonic acid is selected from the group consisting of: methanesulfonic acid, ethanesulfonic acid, trifluoromethanesulfonic acid, p-toluenesulfonic acid, camphorsulfonic acid, benzenesulfonic acid, naphthalene sulfonic and disulfonic acids. More preferably, the sulfonic acid is either methane sulfonic acid or camphorsulfonic acid. Preferably, the inorganic acid is selected from the group consisting of: hydrochloric acid, hydrobromic acid, sulfuric acid, nitric acid, phosphoric acid, perchloric acid, and fluoroboric acid. The more preferred inorganic acid is hydrochloric acid. The more preferred acid is methane sulfonic acid.

Combining the OAN compound of formula V, the solvent and the acid provides a mixture. Preferably, the mixture is maintained at a temperature of about 10° C. to about 60° C., more preferably, at a temperature of about 20° C. to about 50° C., most preferably at a temperature of about 30° C. to about 40° C. The mixture is preferably maintained at such temperature for about 1 hour to about 24 hours, and more preferably, for about 2 to about 12 hours. Maintaining the reaction mixture is preferably done while stirring.

Preferably, reacting the OAN compound with an acid provides the corresponding OAN-salt of formula Vs. Preferably, the OAN-salt of formula Vs precipitates from the reaction mixture. Preferably, in the process of purifying the OAN compound of formula V, the precipitate is reacted with a base providing the OAN compound of formula V back again. Preferably, the precipitate is recovered prior to reacting with a base.

Preferably, the base is selected from the group consisting of sodium hydroxide, sodium carbonate, sodium bicarbonate, potassium hydroxide, potassium carbonate and potassium bicarbonate. More preferably, the base is sodium bicarbonate.

The process for preparing an OAN-salt of formula Vs may further comprise a process for converting it to a DLS-salt of formula VIIIs.

The present invention provides a process for the preparation of a HAN compound of formula VI

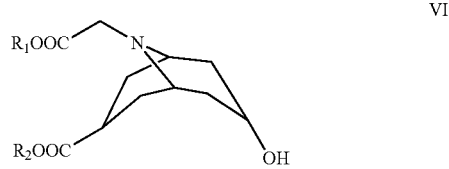

comprising combining an OAN salt of formula Vs, a reducing agent, and a solvent selected from the group consisting of water, water miscible organic solvents and mixtures thereof to obtain the HAN compound of formula VI.

Preferably, the OAN-salt of formula Vs is OAN-MsOH. When the OAN-salt is used as a starting material, it is combined with a water miscible organic solvent, providing a suspension. Preferably, the suspension is prepared at a temperature of about 15° C. to about 35° C., preferably of about 20° C. to about 25° C. Optionally, the OAN compound of formula V may be used as a starting material. When, the OAN compound of formula V is used as a starting material, it is combined with a water miscible organic solvent, providing a solution. Preferably, the water miscible organic solvent is a $C_{1-4}$ alcohol, more preferably, a $C_{1-3}$ alcohol, most preferably, a $C_{1-2}$ alcohol. A preferred $C_{1-2}$ alcohol is methanol.

Preferably, the reducing reagent is a metal hydride complex, preferably lithium borohydride, selectricde or sodium borohydride, more preferably, sodium borohydride. The reducing agent may be used in a basic aqueous solution or as a solid. When the OAN compound of formula V is the starting material, a basic aqueous solution of the reducing agent may be used. Preferably, the basic aqueous solution is an aqueous solution of an alkali hydroxide, more preferably an aqueous solution of sodium hydroxide. Preferably, the basic aqueous solution contains about 30% to about 50% by weight, preferably about 30%, of sodium hydroxide.

Preferably, the solution of the OAN compound of formula V in a $C_{1-4}$ alcohol and the basic aqueous solution of the reducing agent are combined at a temperature of about 0° C. to about 10° C., preferably about 0° C. to about 5° C. Preferably, the solution of the reducing reagent is added drop-wise to the solution of the OAN compound in a $C_{1-4}$ alcohol.

When the OAN-salt of formula Vs is the starting material, a solid reducing agent may be used. Preferably, the suspension of the OAN-salt of formula Vs in a $C_{1-4}$ alcohol and the reducing agent are combined at a temperature of about 15° C. to about 35° C., preferably about 20° C. to about 25° C. Preferably, the reducing reagent is added portion-wise to the suspension of the OAN-salt in a $C_{1-4}$ alcohol. Preferably, the portion-wise addition of the reducing agent is done while maintaining the temperature at about 15° C. to about 35° C., preferably about 25° C. to about 35° C.

Combining the above substances leads to a mixture. Preferably, the mixture is maintained for about a half hour to about 2 hours, preferably for about a half hour to about an hour at such temperature, prior to recovering the HAN compound of formula VI.

When the OAN compound of formula V is used as a starting material, the mixture is maintained at a temperature of about 0° C. to about 5° C., for about an hour, and when the starting material is OAN-salt of formula Vs, the mixture is maintained at a temperature of about 25° C. to about 35° C., for about a half an hour. The reaction may be monitored by TLC using ethylacetate as an eluent.

The process for preparing the HAN compound of formula VI may further comprise a recovery step. The recovery may be carried out by any known method. The HAN compound of formula VI may be recovered by a process comprising adding an acid, preferably a water miscible organic acid, more preferably acetic acid, to the reaction mixture, to give a precipitate. The precipitate is then combined with water and with a halogenated hydrocarbon, preferably a $C_{1-2}$ halogenated hydrocarbon, to give a solution, optionally followed by filtration. The aqueous phase is then extracted, and the solvent is evaporated form the combined organic phase, providing a crude HAN compound. Optionally, after adding acetic acid, the mixture is evaporated and the residue is combined with ethylacetate. The undissolved particles are then, filtered off, and the filtrate is concentrated, providing a crude HAN compound.

The present invention further provides a process for the preparation of a HAN-salt of formula VIs,

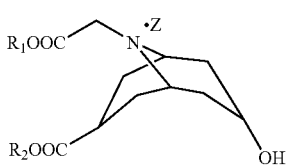

VIs comprising reacting the HAN compound of formula VI,

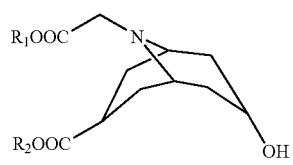

VI an acid, and an organic solvent selected from the group consisting of a $C_{1-4}$ alcohol, a $C_{2-8}$ ester, a linear, branched or cyclic $C_{2-8}$ ether, a $C_{3-6}$ ketone and a $C_{5-8}$ aliphatic hydrocarbon, a $C_{1-8}$ halogenated hydrocarbon, a $C_{1-4}$ nitroalkane, a $C_{1-4}$ alkylcyanide, a $C_{6-8}$ aromatic hydrocarbon, a $C_{3-10}$ amide, and mixtures thereof, wherein, Z, $R_1$ and $R_2$ are described before.

When $R_1$ and $R_2$ are methyl, said HAN compound of formula VI corresponds to HAN of the following formula,

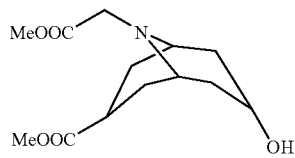

and when $R_1$ and $R_2$ are methyl Z is methane sulfonic acid, said HAN-salt of formula VIs corresponds to HAN-MsOH of the following formula.

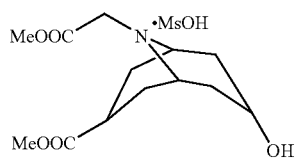

The process for preparing the HAN compound of formula VI may further comprise a process for converting it to a DLS-salt of formula VIIIs.

The present invention also provides a process for purifying the HAN compound of formula VI comprising combining the HAN compound of formula VI, an acid, and an organic solvent selected from the group consisting of a $C_{1-4}$ alcohol, a $C_{2-8}$ ester, a linear, branched or cyclic $C_{2-8}$ ether, a $C_{3-6}$ ketone and a $C_{5-8}$ aliphatic hydrocarbon, a $C_{1-8}$ halogenated hydrocarbon, a $C_{1-4}$ nitroalkane, a $C_{1-4}$ alkylcyanide, a $C_{6-8}$ aromatic hydrocarbon, a $C_{3-10}$ amide, and mixtures thereof; and adding a base.

The HAN compound of formula VI used as a starting material may be a crude HAN compound.

Preferably, the HAN compound of formula VI is dissolved in an organic solvent selected from the group consisting of a $C_{1-4}$ alcohol, a $C_{2-8}$ ester, linear, branched or cyclic $C_{2-8}$ ethers, a $C_{3-6}$ ketone and a $C_{5-8}$ aliphatic hydrocarbon, a $C_{1-8}$ halogenated hydrocarbon, a $C_{1-4}$ nitroalkane, a $C_{1-4}$ alkylcyanide, a $C_{6-8}$ aromatic hydrocarbon, a $C_{3-10}$ amide, and mixtures thereof, prior to adding the acid.

Preferably, the $C_{1-4}$ alcohol is a $C_{1-3}$ alcohol. Preferably, the $C_{1-3}$ alcohol is methanol, ethanol, n-propanol, or isopropanol. A preferred $C_{2-8}$ ester is a $C_{2-6}$ ester, more preferably a $C_{4-6}$ ester. A preferred $C_{4-6}$ ester is ethyl acetate, propyl acetate, butyl acetate, or isobutyl acetate. A preferred linear, branched or cyclic $C_{2-8}$ ether is a $C_{2-7}$ ether, more preferably a $C_{2-6}$ ether. A preferred $C_{2-6}$ ether is tetrahydrofuran, 1,4-dioxane, diisopropyl ether, or t-butyl methyl ether. Preferably, the $C_{3-6}$ ketone is a $C_{3-5}$ ketone. Preferably, the $C_{3-5}$ ketone is acetone, methyl ethyl ketone (2-butanone), 2-pentanone, 3-pentanone, or 3,3-dimethyl-2-butanone. Preferably, the $C_{5-8}$ aliphatic hydrocarbon is a $C_{5-7}$ aliphatic hydrocarbon, more preferably a $C_{6-7}$ aliphatic hydrocarbon. A preferred $C_{6-7}$ aliphatic hydrocarbon is either n-hexane, or n-heptane. A preferred $C_{1-8}$ halogenated hydrocarbon is a $C_{1-6}$ halogenated hydrocarbon, more preferably a $C_{1-4}$ halogenated hydrocarbon, most preferably a $C_{1-2}$ halogenated hydrocarbon. A preferred $C_{1-2}$ halogenated hydrocarbon is dichloromethane, dichloroethane, or chloroform. A preferred $C_{1-4}$ nitroalkane is a $C_{1-2}$ nitroalkane. Preferably, the $C_{1-2}$ nitroalkane is nitromethane or nitroethane. Preferably, the $C_{1-4}$ alkylcyanide is a $C_{1-3}$ alkylcyanide. A preferred $C_{1-3}$ alkylcyanide is either acetonitrile or propionitrile. A preferred $C_{6-8}$ aromatic hydrocarbon is a $C_{6-7}$ aromatic hydrocarbon. Preferably, the $C_{6-7}$ aromatic hydrocarbon is toluene. A preferred $C_{3-10}$ amide is a $C_{3-6}$ amide. Preferably, the $C_{3-6}$ amide is dimethylformamide. The more preferred solvent for dissolving the HAN compound of formula VI is a $C_{2-4}$ ester, most preferably, ethylacetate.

Preferably, the acid is the same as the acid in the process for preparing the purified OAN compound of formula V. The more preferred acid is methane sulfonic acid.

Combining the HAN compound of formula VI, the solvent and the acid provides a mixture. Preferably, the mixture is maintained at a temperature of about 10° C. to about 60° C., more preferably, at a temperature of about 20° C. to about 50° C., most preferably at a temperature of about 30° C. to about 40° C. The mixture is preferably maintained at such temperature for about 0.5 hours to about 24 hours, and more preferably for about 1 hour to about 3 hours, most preferably for about 2 hours. Maintaining the reaction mixture is preferably done while stirring.

Preferably, reacting the HAN compound with an acid provides a corresponding HAN-salt of formula VIs. Preferably, the HAN-salt of formula VIs precipitates from the reaction mixture. Preferably, in a process for purifying the HAN compound of formula VI, the HAN-salt of formula VIs is reacted with a base, providing the HAN compound of formula VI back again. Preferably, the precipitate is recovered prior to reacting with a base.

Preferably, the base is selected from the group consisting of sodium hydroxide, sodium carbonate, sodium bicarbonate, potassium hydroxide, potassium carbonate and potassium bicarbonate. More preferably, the base is sodium bicarbonate.

The process for preparing a HAN-salt of formula VIs may further comprise a process for converting it to a DLS-salt of formula VIIIs.

In one embodiment the present invention provides a process for the preparation of a PAN compound of formula VII

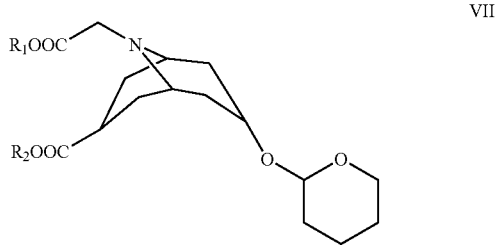

VII comprising a) preparing a 7-alkoxycarbonyl-9-(alkoxycarbonylmethyl)-9-azabicyclo[3.3.1]nonane-3-ol compound (a HAN compound) of formula VI

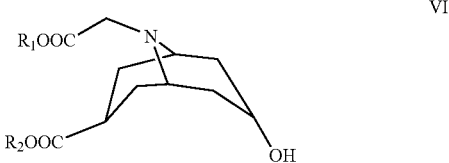

VI comprising combining an OAN compound of formula V or salts thereof, a reducing agent, and a solvent selected from the group consisting of water, water miscible organic solvents and mixtures thereof to form mixture to obtain an HAN compound of formula VI;

b) mixing the HAN compound of formula VI, a substance comprising an ether protecting group, an acid, and a $C_{3-8}$ ester to form a mixture; and c) adding a base to the mixture to obtain the PAN compound of formula VII, wherein $R_1$ and $R_2$ are independently a $C_{1-6}$ alkyl or a $C_{6-8}$ aryl.

Preferably, the substance comprising an ether protecting group is a cyclic ether, more preferably, tetrahydropyran.

Preferably, the $C_{3-8}$ ester is a $C_{3-6}$ ester, more preferably, a $C_{3-5}$ ester, most preferably, a $C_{3-4}$ ester. Preferably, the $C_{3-4}$ ester is ethylacetate.

Preferably, the acid is the same as the acid in the process for preparing the purified OAN compound of formula V. The more preferred acid is methane sulfonic acid.

Preferably, a solution of the acid in a $C_{3-8}$ ester is added drop-wise, to a solution of the HAN compound of formula VI and a substance comprising an ethereal protecting group. Preferably, the drop-wise addition is done at a temperature of about 30° C. to about 50° C., preferably at a temperature of about 40° C. to about 45° C. The addition may lead to a temperature increase to about 50° C. to about 55° C., and optionally, to crystallization of a solid; wherein, the solid is a salt of the PAN compound, preferably, a mesylate salt when the acid is methane sulfonic acid.

Combining the HAN compound of formula VI, an ether protecting group, an acid and a $C_{3-8}$ ester, provides a mixture. Preferably, the mixture is heated to a temperature of about 40° C. to about 60° C., preferably of about 50° C. to about 55° C. Preferably, the mixture is heated for a period of about 15 minutes to about 1 hour, more preferably for about 30 minutes.

The progress of the reaction may be monitored by TLC.

Preferably, the heated mixture is cooled to a temperature of about 5° C. to about 20° C., preferably about 10° C. to about 15° C. Preferably, the mixture is cooled for a period of about 1 to 4 hours, preferably about 2 hours, to complete the precipitation of a PAN salt, prior to addition of the base. A PAN salt may be recovered by drying the precipitate obtained without adding a base.

Preferably, the base is added with water and a $C_{3-8}$ ester, thus creating a two phase system. Preferably, the base is an inorganic base, more preferably selected from sodium hydroxide, sodium carbonate, sodium bicarbonate, potassium hydroxide, potassium carbonate and potassium bicarbonate, and most preferably, an aqueous solution of sodium bicarbonate.

The PAN compound may be recovered by a process comprising phase separation, followed by washing the organic phase with water and brine, and evaporating the solvent, to give the PAN compound.

The PAN compound of formula VII can be used in the next step, the preparation of the PQO compound of formula IX, without purification.

After obtaining the PAN compound of formula VII, the PQO compound of formula IX preferably to a temperature of about 15° C. to about 25° C., prior to the addition of the acid.

Preferably, the weak acid has a pKa of not less than 1, preferably of 1 to 7, more preferably of 2 to 7, most preferably of 3 to 6. Prefereably, the weak acid is selected from the group consisting of acetic acid, formic acid, propionic acid, maleic acid, fumaric acid, succinic acid, oxalic acid, tartaric acid, citric acid, mandelic acid, benzoic acid, and salicylic acid. The more preferred acid is acetic acid, more preferably aqueous acetic acid.

When the acid is added, the pH is adjusted to 5-6 with a base. Preferably, the base is selected from the group consist-

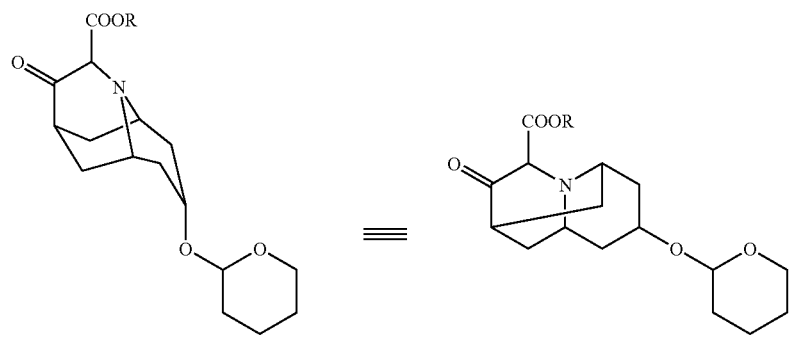

IX may be prepared by a process comprising mixing the PAN of formula VII, a metal alkoxide, and a polar aprotic organic solvent forming a mixture; heating the mixture; and reacting the mixture with a weak acid, to form a mixture; and adding a base, wherein, R is a $C_{1-6}$ alkyl or a $C_{6-8}$ aryl, preferably, a $C_{1-4}$ alkyl, more preferably, methyl.

A preferred polar a-protic organic solvent is selected from the group consisting of a $C_{2-8}$ ether having a boiling point of about 60° C. to about 100° C. Preferably, the $C_{2-8}$ ether is tetrahydrofuran (referred to as THF), 2-methyltetrahydrofuran, tetrahydropyrane, monoglyme, diisopropyl ether, or methyl t-butyl ether. The more preferred polar aprotic organic solvent is THF. Preferably, the PAN compound of formula VII is dissolved in a polar aprotic organic solvent selected from the group consisting of a $C_{2-8}$ ether, prior to adding the metal alkoxide.

Preferably, the metal alkoxide is selected from a group consisting of lithium alcoholates, sodium alcoholates and potassium alcoholates; wherein the alcoholate moiety contains 1 to 4 carbons. More preferably, the alkoxide is potassium tert-butoxide.

Combining the PAN compound of formula VII, with the polar a-protic organic solvent and the metal alkoxide provides a reaction mixture, which is heated to a temperature of about 40° C. to about 120° C., more preferably, to a temperature of about 60° C. to about 80° C. The reaction mixture is preferably heated for a period of about 0.5 hours to about 8 hours, and more preferably, for about 1 hour to about 3 hours, most preferably about 2 hours. Heating the reaction mixture is preferably done while stirring. While heating, the reaction mixture is concentrated, preferably by distillation of the polar a-protic organic solvent.

The heated concentrated reaction mixture is, preferably, cooled to a temperature of about 0° C. to about 30° C., more ing of sodium hydroxide, sodium carbonate, sodium bicarbonate, potassium hydroxide, potassium carbonate and potassium bicarbonate.

Preferably, the PAN compound of formula VII may be converted directly to HQO of formula II

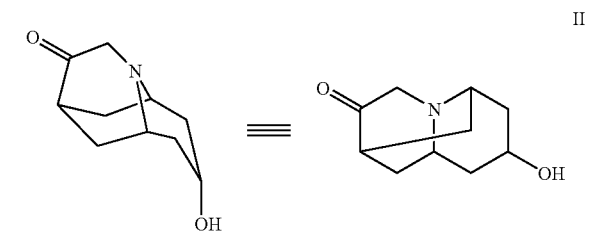

II without the isolation of a PQO compound of formula IX. Preferably, the reaction may include the same steps, described in the process for preparing the PQO compound but using a strong acid instead of a weak acid, and heating the mixture.

The process for preparing the PQO compound and HQO may further comprise a recovery step. Recovery of the PQO compound and of HQO may include the steps of adding a base to the acidic mixture obtained from preparing the PQO compound or HQO, extracting the aqueous phase and evaporating the solvent. Preferably, the base is selected from the group consisting of sodium hydroxide, sodium carbonate, sodium bicarbonate, potassium hydroxide, potassium carbonate and potassium bicarbonate. The recovered products may be further purified by column chromatography, using a mixture of dichloromethane and a $C_{1-2}$ alcohol as an eluent.

The process for preparing the PQO compound of formula IX may further comprise a process for converting it to a DLS-salt of formula VIIIs.

The present invention further provides a process for the preparation of HQO-salt of formula IIs

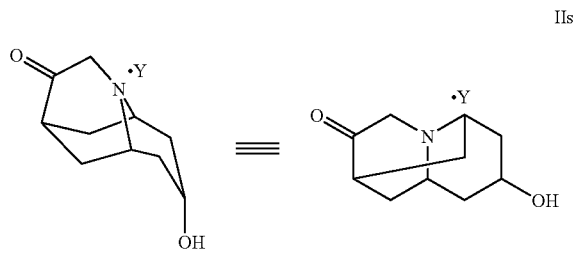

comprising mixing a PAN compound of formula VII,

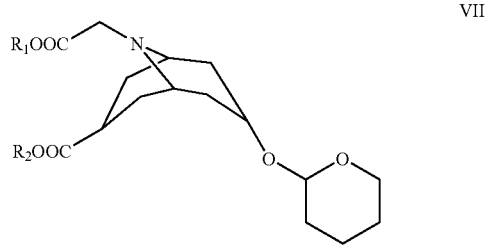

a metal alkoxide, and a polar a-protic organic solvent forming a mixture; heating the mixture, and adding to the mixture an acid selected from the group consisting of: hydrochloric acid, hydrobromic acid, sulfuric acid, nitric acid, phosphoric acid, and perchloric acid, preferably HCl, wherein, $R_1$, $R_2$ and Y are described before.

When $R_1$ and $R_2$ are methyl, said PAN compound of formula VII corresponds to PAN of the following formula,

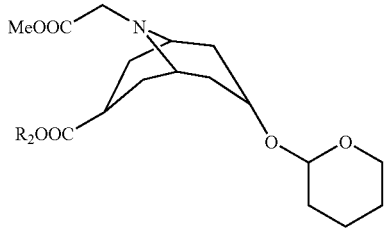

and, when Y is HCl, said HQO-salt of formula IIs corresponds to HQO-HCl of the following formula.

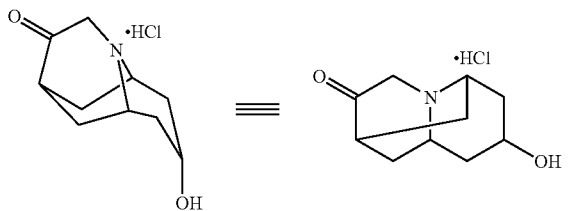

The present invention also provides a process for purifying HQO of formula II comprising mixing the PAN compound of formula VII, a metal alkoxide, and a polar a-protic organic solvent forming a mixture; reacting the mixture with an acid selected from the group consisting of: hydrochloric acid, hydrobromic acid, sulfuric acid, nitric acid, phosphoric acid, and perchloric acid, and adding a base.

A preferred polar a-protic organic solvent is selected from the group consisting of a $C_{2-8}$ ether having a boiling point of about 60° C. to about 100° C. Preferably, the $C_{2-8}$ ether is tetrahydrofuran (referred to as THF), 2-methyltetrahydrofuran, tetrahydropyrane, monoglyme, diisopropyl ether, or methyl t-butyl ether. The more preferred polar aprotic organic solvent is THF. Preferably, the PAN compound of formula VII is dissolved in a polar aprotic organic solvent selected from the group consisting of a $C_{2-8}$ ether, prior to adding the metal alkoxide.

Preferably, the metal alkoxide is selected from a group consisting of lithium alcoholates, sodium alcoholates and potassium alcoholates; wherein the alcoholate moiety contains 1 to 4 carbons. More preferably, the alkoxide is potassium tert-butoxide.

Combining the PAN compound of formula VII, with the polar a-protic organic solvent and the metal alkoxide provides a reaction mixture, which is heated to a temperature of about 40° C. to about 120° C., more preferably, to a temperature of about 60° C. to about 80° C. The reaction mixture is preferably heated for a period of about 0.5 hours to about 8 hours, and more preferably, for about 1 hour to about 3 hours, most preferably about 2 hours. Heating the reaction mixture is preferably done while stirring. While heating, the reaction mixture is concentrated, preferably by distillation of the polar a-protic organic solvent.

The heated concentrated reaction mixture is, preferably, cooled to a temperature of about 0° C. to about 30° C., more preferably to a temperature of about 15° C. to about 25° C., prior to the addition of the acid.

Prior to the addition of the acid, water is combined with the cooled reaction mixture. The more preferred acid is either hydrochloric acid or camphorsulfonic acid. When the acid is added, an acidic mixture, preferably, having a pH of about 0.5 to about 3, more preferably of about 1 to about 2, is obtained.

The remaining polar a-protic organic solvent is removed from the acidic mixture, more preferably by distillation, to obtain a concentrated acidic mixture, prior to heating. The concentrated acidic mixture is heated, preferably, to about a reflux temperature, more preferably to a temperature of about 80° C. to about 100° C. The heated mixture is preferably heated for a period of about 3 hours to about 24 hours, and more preferably, for about 4 hour to about 8 hours, most preferably for about 6 hours. Heating the mixture is preferably done while stirring.

The process for preparing a HQO-salt of formula IIs may further comprise a recovery step. HQO-salt of formula IIs may be recovered by a process comprising cooling the heated mixture to a temperature of about 0° C. to about 30° C., more preferably, to a temperature of about 15° C. to about 25° C., and removing the black sticky material, formed during the reaction, preferably by decantation of the liquid part of the mixture, to obtain a solution. The solution is then evaporated and isopropanol is added, to obtain a precipitate of the salt.

Preferably, reacting the PAN compound with an acid provides the corresponding salt HQO-salt of formula IIs. Preferably, the HQO-salt of formula IIs precipitates from the reaction mixture. Preferably, the HQO-salt of formula IIs is reacted with a base, providing HQO of formula II. Preferably, the precipitate is recovered prior to reacting with a base.

Preferably, the base is selected from the group consisting of sodium hydroxide, sodium carbonate, sodium bicarbonate, potassium hydroxide, potassium carbonate and potassium bicarbonate. The more preferred base is sodium bicarbonate.

The present invention also provides another process for the preparation of a HQO-salt of formula IIs comprising combining HQO, an alcohol and an acid selected from the group consisting of: hydrocloric acid, hydrobromic acid, sulfuric acid, nitric acid, phosphoric acid, perchloric acid, fluoroboric acid, formic acid, acetic acid, propionic acid, trichloroacetic acid, trifluoroacetic acid, maleic acid, fumaric acid, succinic acid, oxalic acid, tartaric acid, citric acid, mandelic acid, benzoic acid, salicylic acid, naphthalene carboxylic and dicarboxylic acids, methanesulfonic acid, ethanesulfonic acid, trifluoromethanesulfonic acid, p-toluenesulfonic acid, benzenesulfonic acid, naphthalene sulfonic, and disulfonic acid, to obtain a HQO salt of formula IIs.

The present invention provides a process for purifying HQO of formula II by a process comprising combining HQO of formula II, an alcohol and an acid selected from the group consisting of: hydrochloric acid, hydrobromic acid, sulfuric acid, nitric acid, phosphoric acid, perchloric acid, fluoroboric acid, formic acid, acetic acid, propionic acid, trichloroacetic acid, trifluoroacetic acid, maleic acid, fumaric acid, succinic acid, oxalic acid, tartaric acid, citric acid, mandelic acid, benzoic acid, salicylic acid, naphthalene carboxylic and dicarboxylic acids, methanesulfonic acid, ethanesulfonic acid, trifluoromethanesulfonic acid, p-toluenesulfonic acid, benzenesulfonic acid, naphthalene sulfonic, and disulfonic acid forming a mixture; and adding a base to obtain purified HQO.

Preferably, the alcohol is a $C_{1-4}$ alcohol, more preferably, ethanol.

Preferably, the acid is an organic acid, more preferably, a sulfonic acid, most preferably, methanesulfonic acid.

The process for preparing a HQO-salt of formula IIs can further comprise a process for converting it to a DLS-salt of formula VIIIs.

HQO-salt of formula IIs may be converted to a DLS-salt of formula VIIIs comprising converting it to the free base, HQO of formula II; reacting HQO with a base to form a reaction mixture; mixing the reaction mixture with an anhydride, indole-3-carboxylic acid, an organic solvent, and a catalyst to form a mixture; and reacting the mixture with an acid, to obtain the DLS-salt of formula VIIIs.

Preferably, the base is selected from the group consisting of sodium hydroxide, sodium carbonate, sodium bicarbonate, potassium hydroxide, potassium carbonate and potassium bicarbonate. The more preferred base is sodium bicarbonate.

Preferably, the organic solvent is selected from the group consisting of a $C_{1-2}$ halogenated hydrocarbon, a $C_{6-8}$ aromatic hydrocarbon, a $C_{1-4}$ nitroalkane, a $C_{14}$ alkyl cyanide, trifluoroacetic acid and mixtures thereof. A preferred $C_{1-2}$ halogenated hydrocarbon is dichloromethane, 1,2-dichloroethane or chloroform, more preferably dichloromethane. A preferred $C_{6-8}$ aromatic hydrocarbon is benzene, toluene or xylol, more preferably toluene. Preferably, the $C_{1-4}$ nitroalkane is a $C_{1-2}$ nitroalkane, either nitromethane or nitroethane, more preferably nitromethane. Preferably, the $C_{1-4}$ alkyl cyanide is a $C_{1-2}$ alkyl cyanide, either acetonitrile or propionitrile, more preferably acetonitrile.

Preferably, the anhydride is either trifluoroaceticanhydride or methyl chlorocarbonate, more preferably, trifluoroaceticanhydride.

Preferably, indole-3-carboxylic acid is added drop-wise, more preferably, over a period of about 10 minutes to about 30 minutes, preferably about 15 minutes.

Preferably, the catalyst is either a saturated trisubstituted amine or an aromatic amine. Preferably, the saturated trisubstituted amine is either a trialkyl amine or 4-dialkylaminopyridine amine. Preferably, the trisubstituted amine is 4-dimethylaminopyridine or diisopropylethylamine, more preferably, 4-dimethylaminopyridine.

Preferably, HQO and the catalyst are added at the same time to a solution of the anhydride, the organic solvent and the 3-indole-carboxylic acid, providing a reaction mixture. Preferably, the reaction mixture is heated to a temperature of about 25° C. to about 40° C., more preferably to about 30° C. to about 35° C., for about 2 to about 18 hours, more preferably for about 2 hours, and preferably while stirring, providing Dolasetron base.

Dolasetron base may be recovered by removing the solvent to obtain a precipitate and filtering off the precipitate.

Dolasetron may be converted to Dolasetron salt by a process comprising combining Dolasetron with an acid. Preferably, Dolasetron may be converted to Dolasetron mesylate monohydrate by a process comprising combining Dolasetron, a mixture of acetone and water, and methane sulfonic acid.

Combining Dolasetron and the mixture of acetone and water provides a suspension, in which the solid dissolves when adding methane sulfonic acid. After complete dissolution, a precipitate of DLS-MsOH is obtained. The precipitate may be maintained in a fridge, and recovered by filtration, washing and drying.

The present invention also provides a process for the preparation of a DLS-salt of formula VIIIs, designated as process No. 1, comprising combining a CCA-ester of formula III, an oxidizing agent selected from the group consisting of: hydroperoxides, dialkyl peroxides, peroxyacids, peroxyesters, diacyl peroxides, persulphate, perborate and perphosphate, a catalyst and a solvent selected from the group consisting of water, water miscible organic solvents and mixtures thereof forming a first intermediate mixture; adding an oxidizing agent, a solvent selected from the group consisting of water and water miscible organic solvent to a first intermediate mixture forming a second intermediate mixture; raising the pH of the second intermediate mixture; reacting the products in the second intermediate mixture with a pH 4 buffer, a glycine $C_{1-4}$ ester or salts thereof, and a substance comprising a carbonyl moiety selected from the group consisting of 1,3-acetonedicarboxylic acids, acetone and a $C_{1-4}$ ester thereof, forming a third intermediate mixture; adding to the third intermediate mixture a reducing agent, and a solvent selected from the group consisting of water, water miscible organic solvents and mixtures thereof, forming a fourth intermediate mixture; mixing the fourth intermediate mixture with an ether protecting group, an acid, and a $C_{3-8}$ ester, forming a fifth intermediate mixture; adding a base to the fifth intermediate mixture; further combining the fifth intermediate mixture with a metal alkoxide and a polar aprotic organic solvent forming a sixth intermediate mixture; heating the sixth intermediate mixture; adding to the sixth intermediate mixture an acid selected from the group consisting of: hydrochloric acid, hydrobromic acid, sulfuric acid, nitric acid, phosphoric acid, and perchloric acid, forming a seventh intermediate mixture; adding a base to the seventh intermediate mixture; further mixing with the seventh intermediate mixture an anhydride, 3-indole carboxylic acid, an organic solvent, and a catalyst; and reacting the product of the previous step with an acid to obtain the DLS-salt of formula VIIIs. Preferably, the acid in the last step is selected from the group consisting of hydrochloric acid, hydrobromic acid, sulfuric acid, nitric acid, phosphoric acid, perchloric acid, fluoroboric acid, formic acid, acetic acid, propionic acid, trichloroacetic acetic, trifluoroacetic acid, maleic acid, fumaric acid, succinic acid, oxalic acid, tartaric acid, citric acid, mandelic acid, benzoic acid, salicylic acid, naphthalene carboxylic and dicarboxylic acids, methanesulfonic acid, ethanesulfonic acid, trifluoromethanesulfonic acid, p-toluenesulfonic acid, camphorsulfonic acid, benzenesulfonic acid, naphthalene sulfonic and disulfonic acids, preferably, methane sulfonic acid. Further, in the above process of preparing a DLS-salt of formula VIIIs the steps of adding a base to the fifth intermediate mixture and to the seventh intermediate mixture are optional.

The process can be illustrated by the following scheme:

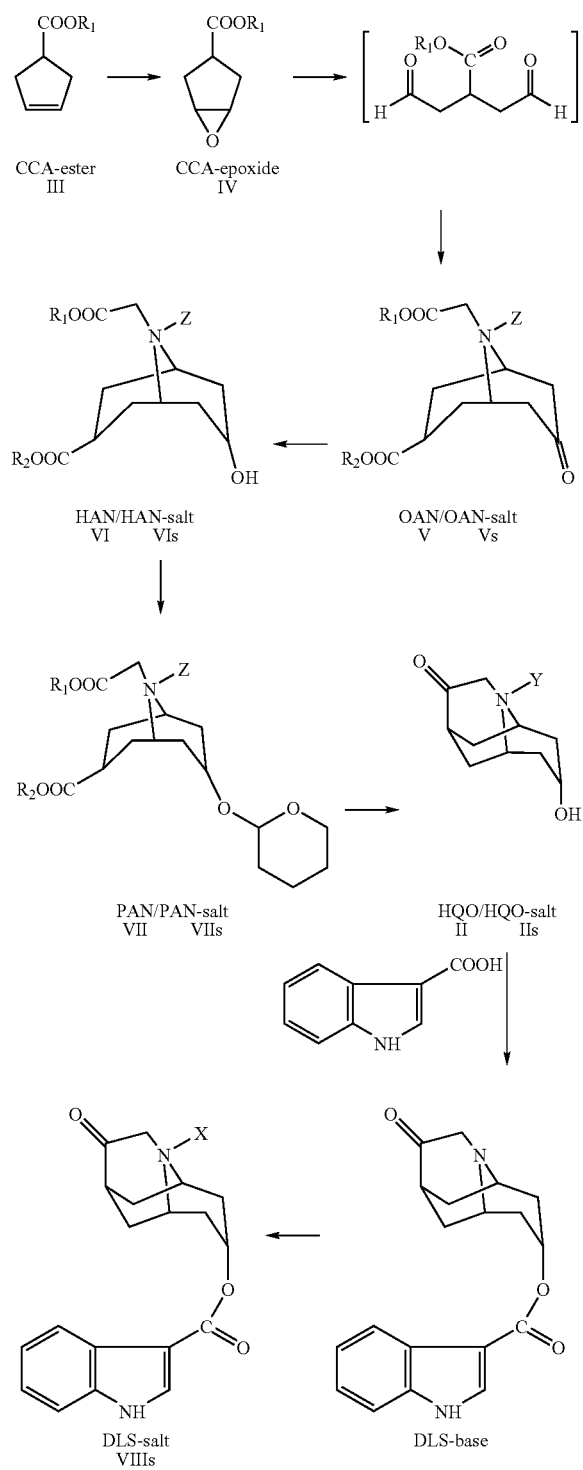

The present invention also provides a process for the preparation of a PivAN compound of formula XIII

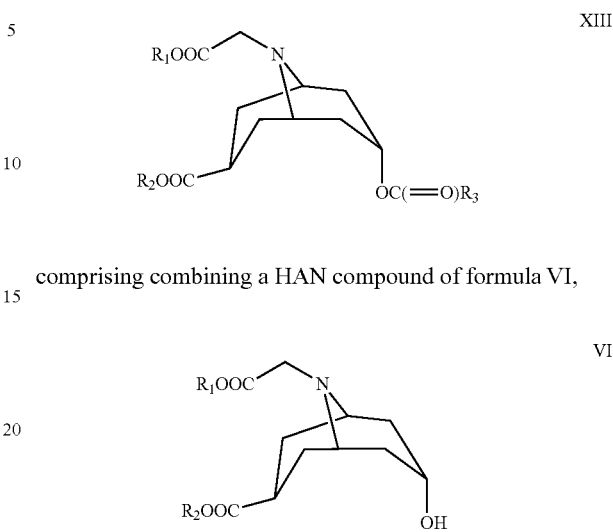

comprising combining a HAN compound of formula VI, an acylating agent selected from a group consisting of: carboxylic acids, carboxylic halogenides, and carboxylic anhydrides, a base, and a solvent selected from the group consisting of a-protic organic solvents and mixtures thereof, forming a mixture to obtain a PivAN compound of formula XIII, wherein, $R_1$ and $R_2$ and $R_3$ are independently a $C_{1-6}$ alkyl or a $C_{6-8}$ aryl, preferably, a $C_{1-4}$ alkyl, more preferably, $R_1$ and $R_2$ are methyl and $R_3$ is tert-butyl.

Preferably, combining the HAN compound of formula VI with a solvent selected from the group consisting of a $C_{1-8}$ halogenated hydrocarbon, a $C_{2-8}$ ester, a $C_{2-8}$ ether, a $C_{3-6}$ ketone, a $C_{6-8}$ aromatic hydrocarbon, a $C_{3-10}$ amide, and mixtures thereof, provides a solution. A preferred $C_{1-8}$ halogenated hydrocarbon is a $C_{1-2}$ halogenated hydrocarbon. Preferably, the $C_{1-2}$ halogenated hydrocarbon is dichloromethane (methylene chloride), 1,2-dichloroethane or chloroform. A preferred $C_{2-8}$ ester is a $C_{4-6}$ ester. Preferably, the $C_{4-6}$ ether is ethyl acetate, n-butyl acetate or isobutyl acetate. A preferred $C_{2-8}$ ether is a $C_{4-6}$ ether. Preferably, the $C_{4-6}$ ester is diethyl ether, diisopropyl ether or tert-butyl methyl ether. A preferred $C_{3-6}$ ketone is a $C_{4-6}$ ketone. Preferably, the $C_{4-6}$ ketone is methyl ethyl ketone (2-butanone), 2-pentanone, 3-pentanone or 3,3-dimethyl-2-butanone. A preferred $C_{6-8}$ aromatic hydrocarbon is a $C_{6-7}$ aromatic hydrocarbon. Preferably, the $C_{6-7}$ aromatic hydrocarbon is toluene. A preferred $C_{3-10}$ amide is a $C_{3-6}$ amide. Preferably, the $C_{3-6}$ amide is dimethylformamide. The preferred solvent is dichloromethane (methylene chloride).

Preferably, the solution is cooled to a temperature of about −5° C. to about 15° C., more preferably, to 0° C. to about 5° C., prior to the addition of the base and of the acylating agent. Preferably, the base is selected from a group consisting sodium hydroxide, sodium carbonate, sodium bicarbonate, potassium hydroxide, potassium carbonate and potassium bicarbonate, trialkyl amines, and N-containing heterocycles. The preferred base is triethylamine.

Preferably, the acylating agent is selected from the group consisting of pivalic acid, an acyl halogenide, and pivalic anhydride. More preferably the acylating agent is an acyl halogenide, even more preferably, the acyl group is pivaloyl. The preferred acylating reagent is pivaloyl chloride.

Preferably, the addition of the base and of the acylating agent provides a mixture. Preferably, the mixture is maintained at a temperature of about 0° C. to about 80° C., more preferably at a temperature of about 20° C. to about 40° C., most preferably at about 20° C. to about 25° C. The mixture is maintained, preferably, for about 1 day to about 20 days, more preferably for about 5 to about 10 days, most preferably for about 6 days.

The progress of the reaction may be monitored by HPLC or by TLC. When monitored by TLC, an eluent of ethyl acetate is used.

The process for preparing the PivAN compound of formula XIII may further comprise a recovery step. The PivAN compound of formula XIII may be recovered by extracting the product with water, and evaporating the solvent.

The PivAN compound of formula XIII can be used in the next step, the preparation of HQO of formula II, without purification.

The process for preparing the PivAN compound of formula XIII may further comprise a process for converting it to a DLS-salt of formula VIIIs.

The present invention further provides a process for the preparation of HQO of formula II

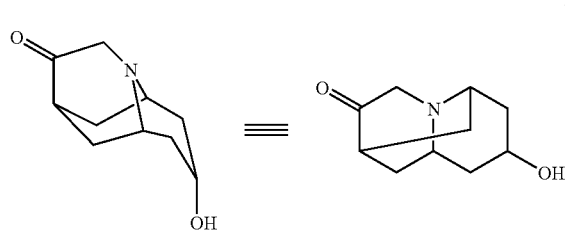

comprising combining a PivAN compound of formula XIII,

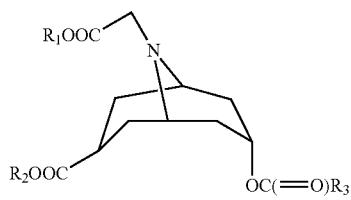

a metal alkoxide, and a polar a-protic organic solvent, forming a mixture; heating the mixture; and adding an acid to obtain HQO of formula II.

Preferably, the acid is selected from the group consisting of: hydrochloric acid, hydrobromic acid, sulfuric acid, nitric acid, phosphoric acid, and perchloric acid, more preferably HCl.

A preferred polar a-protic organic solvent is selected from the group consisting of $C_{2-8}$ ethers having a boiling point of about 60° C. to about 100° C. Preferably, the $C_{2-8}$ ether is tetrahydrofuran (referred to as THF), 2-methyltetrahydrofuran, tetrahydropyrane, monoglyme, diisopropyl ether, or methyl t-butyl ether. The more preferred polar aprotic organic solvent is THF. Preferably, the PivAN compound of formula XIII is dissolved in a polar a-protic organic solvent selected from the group consisting of $C_{2-8}$ ethers, prior to adding the metal alkoxide.

Preferably, the metal alkoxide is selected from a group consisting of lithium alcoholates, sodium alcoholates and potassium alcoholate; wherein the alcoholate moiety contains 1 to 4 carbons. More preferably, the alkoxide is potassium tert-butoxide.

Combining the PivAN compound of formula XIII, the polar a-protic organic solvent and the metal alkoxide provides a reaction mixture, which is heated to a temperature of about 40° C. to about 120° C., more preferably, to a temperature of about 60° C. to about 80° C. The reaction mixture is heated, preferably, for about 0.5 hours to about 8 hours, and more preferably, for about 1 hour to about 3 hours, most preferably for about 2 hours. Heating the reaction mixture is preferably done while stirring. While heating, the reaction mixture is concentrated, preferably, by distillation of the polar aprotic organic solvent.

The heated concentrated reaction mixture is, preferably, cooled to a temperature of about 0° C. to about 30° C., more preferably, to a temperature of about 15° C. to about 25° C., prior to the addition of the acid.

Prior to the addition of the acid, a solvent selected from the group consisting of water, water immiscible organic solvents and mixtures thereof, is combined with the cooled reaction mixture. The more preferred acid is either hydrochloric acid or camphorsulfonic acid. When the acid is added, an acidic mixture, preferably, having a pH of about 0.5 to about 3, more preferably, of about 1 to about 2, is obtained.

The remaining of the polar a-protic organic solvent is removed from the acidic mixture, more preferably, by distillation, to obtain a concentrated acidic mixture, prior to heating. The concentrated acidic mixture is heated, preferably, to about reflux temperature, more preferably, to a temperature of about 80° C. to about 100° C. The heated mixture is maintained, preferably, for about 3 hours to about 24 hours, and more preferably, for about 4 hour to about 8 hours, most preferably for about 6 hours. Heating the mixture is preferably done while stirring.

The process for preparing HQO of formula II may further comprise a recovery step. HQO of formula II may be recovered by cooling the heated acidic solution, adding a base to the cooled acidic solution, extracting the product with a water immiscible organic solvent, and evaporating the water immiscible organic solvent.

Preferably, the heated solution is cooled to a temperature of about 0° C. to about 30° C., more preferably, to a temperature of about 15° C. to about 25° C.

Preferably, a base is added to the cooled solution. Preferably, the base is selected from the group consisting of sodium hydroxide, sodium carbonate, sodium bicarbonate, potassium hydroxide, potassium carbonate and potassium bicarbonate. The more preferred base is sodium hydroxide. Preferably, the addition of the base provides a basic mixture. Preferably, the basic mixture has a pH of about 8 to about 13, more preferably, of about 11 to about 12.

The preferred water immiscible organic solvent is selected from the group consisting of $C_{2-8}$ esters, linear, branched or cyclic $C_{2-8}$ ethers, $C_{3-6}$ ketones, $C_{5-8}$ aliphatic hydrocarbons, $C_{1-8}$ halogenated hydrocarbons, and $C_{6-8}$ aromatic hydrocarbons and mixtures thereof. A preferred $C_{2-8}$ ester is a $C_{4-6}$ ester. Preferably, the $C_{4-6}$ ester is ethyl acetate, n-butyl acetate or isobutyl acetate. A preferred $C_{2-8}$ ether is a $C_{4-6}$ ether. Preferably, the $C_{4-6}$ ether is diethyl ether, diisopropyl ether or t-butyl methyl ether. A preferred $C_{3-6}$ ketone is a $C_{4-6}$ ketone. Preferably, the $C_{4-6}$ ketone is methyl ethyl ketone (2-butanone), 2-pentanone, 3-pentanone or 3,3-dimethyl-2-butanone. A preferred $C_{5-8}$ aliphatic hydrocarbon is a $C_{6-7}$ aliphatic hydrocarbon. Preferably, the $C_{6-7}$ aliphatic hydrocarbon is either n-hexane or n-heptane. A preferred $C_{1-8}$ halogenated hydrocarbon is a $C_{1-2}$ halogenated hydrocarbon. Preferably, the $C_{1-2}$ halogenated hydrocarbon is dichloromethane, 1,2-dichloroethane or chloroform. A preferred $C_{6-8}$ aromatic hydrocarbon is $C_{6-7}$ aromatic hydrocarbon. Preferably, the $C_{6-7}$ aromatic hydrocarbon is toluene. The most preferred water immiscible organic solvent is methylene chloride.

The process for preparing HQO of formula II from a PivAN compound of formula XIII may further comprise a process for converting it to a DLS-salt of formula VIIIs.

The HQO compound of formula II prepared from a PivAN compound of formula XIII may be converted to a DLS-salt of formula VIIIs comprising forming a reaction mixture of HQO in an organic solvent; mixing the reaction mixture with an anhydride, indole-3-carboxylic acid, an organic solvent, and a catalyst to form a mixture; and reacting the mixture with an acid, to obtain the DLS-salt of formula VIIIs.

Preferably, the base is selected from the group consisting of sodium hydroxide, sodium carbonate, sodium bicarbonate, potassium hydroxide, potassium carbonate and potassium bicarbonate. The more preferred base is sodium bicarbonate.

Preferably, the organic solvent is selected from the group consisting of a $C_{1-2}$ halogenated hydrocarbon, a $C_{6-8}$ aromatic hydrocarbon, a $C_{1-4}$ nitroalkane, a $C_{1-4}$ alkyl cyanide, trifluoroacetic acid and mixtures thereof. A preferred $C_{1-2}$ halogenated hydrocarbon is dichloromethane, 1,2-dichloroethane or chloroform, more preferably dichloromethane. A preferred $C_{6-8}$ aromatic hydrocarbon is benzene, toluene or xylol, more preferably toluene. Preferably, the $C_{1-4}$ nitroalkane is a $C_{1-2}$ nitroalkane, either nitromethane or nitroethane, more preferably nitromethane. Preferably, the $C_{1-4}$ alkyl cyanide is a $C_{1-2}$ alkyl cyanide, either acetonitrile or propionitrile, more preferably acetonitrile.

Preferably, the anhydride is either trifluoroaceticanhydride or methyl chlorocarbonate, more preferably, trifluoroaceticanhydride.

Preferably, indole-3-carboxylic acid is added drop-wise, more preferably, over a period of about 10 minutes to about 30 minutes, preferably about 15 minutes.

Preferably, the catalyst is either a saturated trisubstituted amine or an aromatic amine. Preferably, the saturated trisubstituted amine is either a trialkyl amine or 4-dialkylaminopyridine amine. Preferably, the trisubstituted amine is 4-dimethylaminopyridine or diisopropylethylamine, more preferably, 4-dimethylaminopyridine.

Preferably, HQO and the catalyst are added at the same time to a solution of the anhydride, the organic solvent and the 3-indole-carboxylic acid, providing a reaction mixture. Preferably, the reaction mixture is heated to a temperature of about 25° C. to about 40° C., more preferably to about 30° C. to about 35° C., for about 2 to about 18 hours, more preferably for about 2 hours, and preferably while stirring, providing Dolasetron base.

Dolasetron base may be recovered by removing the solvent to obtain a precipitate and filtering off the precipitate.

Dolasetron may be converted to Dolasetron salt by a process comprising combining Dolasetron with an acid. Preferably, Dolasetron may be converted to Dolasetron mesylate monohydrate by a process comprising combining Dolasetron, a mixture of acetone and water, and methane sulfonic acid.

Combining Dolasetron and the mixture of acetone and water provides a suspension, in which the solid dissolves when adding methane sulfonic acid. After complete dissolution, a precipitate of DLS-MsOH is obtained. The precipitate may be maintained in a fridge, and recovered by filtration, washing and drying.

The present invention also provides a process for preparing DLS-salt of formula VIIIs, designated process No. 2, comprising combining a CCA-ester of formula III, an oxidizing agent selected from the group consisting of: hydroperoxides, dialkyl peroxides, peroxyacids, peroxyesters, diacyl peroxides, persulphate, perborate and perphosphate, a catalyst and a solvent selected from the group consisting of water, water miscible organic solvents and mixtures thereof, forming a first intermediate mixture; adding to this first intermediate mixture an oxidizing agent, and a solvent selected from the group consisting of water and water miscible organic solvent to form a second intermediate mixture; raising the pH of the second intermediate mixture; reacting the products in the second intermediate mixture with a pH 4 buffer, a glycine $C_{1-4}$ ester or salts thereof, and a substance comprising a carbonyl moiety selected from the group consisting of 1,3 acetonedicarboxylic acids, acetone and a $C_{1-4}$ ester thereof to form a third intermediate mixture; adding to the third intermediate mixture a reducing agent, and a solvent selected from the group consisting of water, water miscible organic solvents and mixtures thereof to form a fourth intermediate mixture; adding to the fourth intermediate mixture an acylating agent selected from a group consisting of: carboxylic acid, carboxylic halogenides, carboxylic anhydrides, a base, and a solvent selected from a group consisting of aprotic organic solvents and mixtures thereof to form a fifth intermediate mixture; adding to the fifth intermediate mixture a metal alkoxide, and a polar aprotic organic solvent to form a sixth intermediate mixture; heating the sixth intermediate mixture, and adding an acid selected from the group consisting of: hydrochloric acid, hydrobromic acid, sulfuric acid, nitric acid, phosphoric acid, and perchloric acid to form a seventh intermediate mixture; mixing the seventh intermediate mixture with an anhydride, 3-indole carboxylic acid, an organic solvent, and a catalyst; and reacting the product of the previous step with an acid to obtain the DLS-salt of formula VIIIs.

The process can be illustrated by the following scheme:

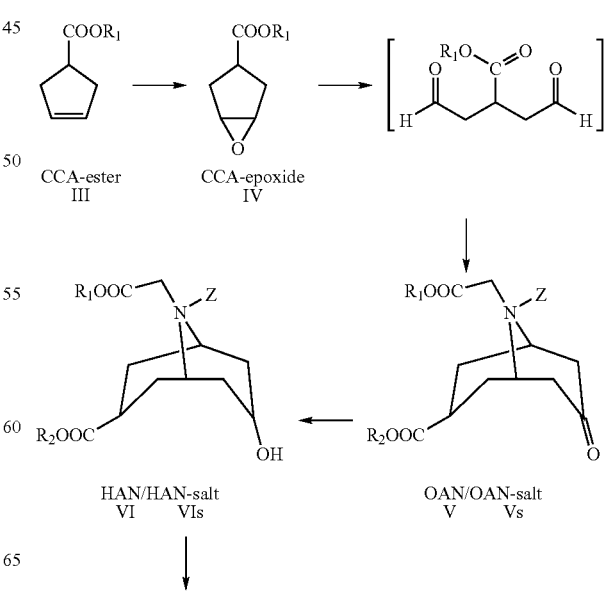

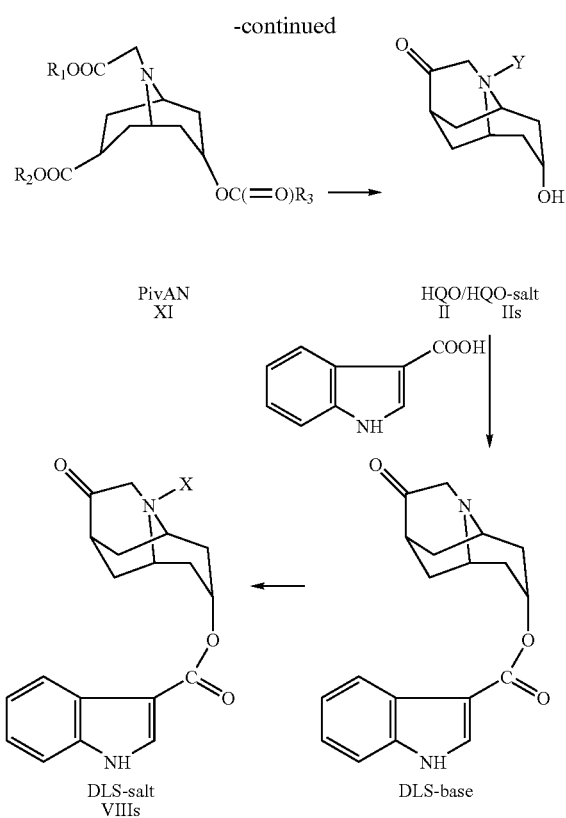

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to limit its scope in any way.

EXAMPLES

Example 1

Preparation of CCA-epoxide of Formula IV

CCA-Me ester (37.8 g, 0.3 mol) was dissolved in 60 ml of methanol followed by the addition of hydrogen peroxide (30-35%, 43 ml, 1.3 equiv.) and sodium tungstate dihydrate (2 g, 2 mol %). The yellow reaction mixture was refluxed slightly (at 60-65° C.) for 2-4 hours until the reaction was completed (GC or TLC: eluent n-hexane-ethyl acetate 1:1, visualized by iodine). After cooling it was extracted with methylene chloride (3×100 ml). The combined organic phases were dried on sodium sulfate and evaporated to dryness. The product was 40.5 g colorless oil (95% yield).

Example 2

Preparation of OAN of Formula V

To a well-stirred solution of periodic acid (32 g, 0.14 mol) in water (200 ml) was added CCA-epoxide (19 g, 0.14 mol), and the reaction mixture was stirred at 10-15° C. for 1 hour. After completion, the reaction mixture having a pH of 1, was cooled and the pH was adjusted to 3.5-4 by the addition of OH-resin (or poly(4-vinylpyridine)), followed by stirring the mixture for 10-15 min at room temperature. The solid material was filtered through a layer of Celite and washed with water (2×150 ml).

To the aqueous solution were added sequentially at room temperature (86 g, 0.42 mol, 3 equiv) potassium hydrogen phthalate, (21 g, 0.17 mol, 1.2 equiv) glycine methyl ester hydrochloride and (25 g, 0.17 mol, 1.2 equiv) 1,3-acetonedicarboxylic acid. The dark red reaction mixture was stirred at room temperature for 18 h (overnight). The undissolved solid was filtered through a layer of Celite, washed with a small volume of water (2×50 ml). To the solution was added, in portions, solid sodium hydrogen carbonate (until pH 7.5-8), then the solution was extracted with isobutyl acetate (5×200 ml). The combined organic phases were dried on sodium sulfate and evaporated to dryness or to a reduced volume of about 40 ml. TLC: n-hexane-ethyl acetate 1:1, visualized by UV-light and/or iodine.

Example 3

Preparation of OAN-MsOH Salt of Formula Vs

Crude OAN (600 g) was dissolved in isopropanol (3 L) at room temperature followed by the addition of (144 ml, 1 equiv) methanesulfonic acid, under stirring. The mixture was warmed to 30-40° C., and stirred for overnight. The precipitated oil solidified. The salt was filtered at room temperature, washed with isopropanol (600+2×300 ml) and dried.

The overall yield (from CCA-epoxide): 35-40% (purity: <90%).

Example 4

Preparation of OAN-MsOH Salt of Formula Vs

OAN solution in isobutyl acetate (1.2 L, containing 600 g of OAN) was combined with ethanol (1.2 L) at room temperature followed by the addition of (144 ml, 1 equiv) methanesulfonic acid, under stirring. The mixture was stirred for 3 hours. The salt was filtered, washed with a mixture of isobutyl acetate-ethanol 1:1 (12×300 ml) and dried.

The overall yield (from CCA-epoxyide): 35-40%.

Example 5

Preparation of HAN of Formula VI

Sodium borohydride (71 g, 1.4 equiv.) was dissolved in a mixture of water (500 ml) and aqueous solution of sodium hydroxide (30%, 14 ml). OAN (361 g, 1.34 mol) was dissolved in methanol (3.6 L), and the solution was cooled to 0-5° C. The solution of sodium borohydride was added dropwise to the solution of OAN in methanol, and the mixture was stirred at 0-5° C. for about 1 hour. The reaction was monitored by TLC (eluent: ethyl acetate). After completion of reaction acetic acid (80 ml) was added under stirring while cooling (foaming, warming and precipitating). Water (0.5 L) and methylene chloride (1 L) were added (filtration can be necessary). The aqueous phase was extracted with (2×1 L) of methylene chloride. The combined organic phases were dried on sodium sulfate and evaporated to dryness. The yield was 70%.

Example 6

Preparation of HAN of Formula VI (14.6 g, 40 mmol) OAN-MsOH was suspended at 20-25° C. in (300 ml) ethanol, then to this suspension (4.2 g, 2.8 equiv) sodium borohydride was added in portions in order to keep the inner temperature between 25-35° C. After addition of the reducing agent the reaction mixture was stirred for additional 30 minutes. The conversion was monitored by TLC (eluent: ethyl acetate), when it was complete (4.5 ml) acetic acid was added (pH 6-7) and the mixture was evaporated to dryness on rotavapor at 35-40° C. The residue was mixed with ethyl acetate (60 ml), the unsolved material was filtered off and the filtered material was washed with ethyl acetate (2×20 ml). The filtrate was concentrated on rotavapor at 35-40° C., to obtain 10.2 g (94%) of crude HAN.

Example 7

Preparation of HAN-MsOH Salt of Formula VIs

Crude HAN (17 g) was dissolved in ethyl acetate (100 ml) at room temperature and (3.6 ml, 1.1 equiv) of methanesulfonic acid was added under stirring. The mixture was heated to 30-40° C., and was stirred for 2 hours. The precipitated oil solidified. The salt was filtered at room temperature, washed with ethyl acetate (2×30 ml) and dried. Yield was 80%.

Example 8

Preparation of PAN of Formula VII

Crude HAN (about 70 a % purity, 245 g) and dihydropyran (230 ml, 2.7 equiv) was dissolved in ethyl acetate (500 ml), the solution was heated to 40-45° C. A solution of methanesulfonic acid (66 ml, 1.1 equiv) in ethyl acetate (1000 ml) was added dropwise. The temperature was allowed up to 50-55° C.

The product started to crystallize during the addition. The mixture was stirred at 50-55° C. for 30 minutes (TLC monitoring, eluent: ethyl acetate), then cooled to 10-15° C. and stirred for 2 hours. The mesylate salt of PAN was filtered off, washed with ethyl acetate (2×200 ml). The wet salt was added to a mixture of sodium hydrogen carbonate (80 g), water (500 ml), and ethyl acetate (2000 ml) under stirring. After phase separation the organic phase was washed with water (500 ml), and brine (500 ml). The organic phase was dried on sodium sulfate, evaporated to dryness. The crude PAN base is 184 g almost colorless oil (yield: 82% yield, purity: 95%).

Example 9

Preparation of HQO of Formula II

PAN-base (183 g, 0.51 mol) was dissolved in tetrahydrofuran (2.5 L) and potassium tert-butoxide (78.5 g, 1.4 equiv) were added under stirring. The solution was heated to reflux for 2 hours, and 1.25 L of tetrahydrofuran was distilled out during this reflux period. The mixture was cooled to room temperature. Water (780 ml) was added, the pH was adjusted to 1 with concentrated HCl (about 130 ml). The rest of tetrahydrofuran was distilled out, and the mixture was refluxed for 6 hours, then cooled to room temperature. The solution was decanted from the black sticky material formed during the reaction. The pH of the solution was adjusted to 12 by addition of solid sodium hydroxide (about 50 g) under cooling, then saturated with NaCl. The solution was extracted with ethyl acetate (5×1600 ml). The combined organic phase was dried on sodium sulfate, and evaporated to dryness. The residue was 72 g brownish sticky-solid.

The crude product was treated with isobutyl acetate (144 m), the solid part was filtered off and washed with this solvent. The yield is 36 g (39%, purity: 99%).

The mother liquor was purified by column chromatography on silica (eluent: methylene chloride-ethanol 1:1 $R_f$ 0.3) to increase the yield to 57%.

Example 10

Preparation of HQO-HCl Salt of Formula IIs

PAN-base (7.1 g, 20 mmol) was dissolved in tetrahydrofuran (100 ml) and potassium tert-butoxide (4.5 g, 2 equiv) was added under stirring. The solution was heated to reflux for 2 hours, and 50 ml of tetrahydrofuran were distilled out during this reflux period. The mixture was cooled to room temperature. Water (100 ml) were added, the pH was adjusted to 1 with concentrated HCl (about 10 ml). The rest of tetrahydrofuran was distilled out, and the mixture was refluxed for 6 hours, then cooled to room temperature. The solution was decanted from the black sticky material formed during the reaction. The solution was evaporated to dryness and isopropanol (50 ml) was added to the residue. The salt was filtered at room temperature, washed with isopropanol (2×10 ml) and dried. Yield is 34%.

Example 11

Preparation of HQO-CSA Salt of Formula IIs

To a solution of HQO (0.18 g, 1 mmol) in (3 ml) ethanol was added camphorsulfonic acid (0.23 g) in (2.5 ml) ethanol. The mixture was stirred for 20 minutes, filtered, then the solid material was washed with ethyl acetate and dried.

Example 12

Preparation of PQO of Formula IX

PAN-base (7.1 g, 20 mmol) was dissolved in tetrahydrofuran (100 ml) and potassium tert-butoxide (4.5 g, 2 equiv) was added under stirring. The solution is heated to reflux for 2 hours, and 50 ml of tetrahydrofuran was distilled out during this reflux period. The mixture was cooled to room temperature. Aqueous acetic acid (3 ml of acetic acid in 80 ml of water) was added, and then the pH was adjusted to 5-6 with sodium hydrogencarbonate. The aqueous phase was extracted with ethyl acetate and dichloromethane, respectively. The combined organic phases were dried on sodium sulfate and evaporated to dryness.

The residue was purified by column chromatography on silica (eluent: methylene chloride-methanol 19:1) to obtain 3.6 g (56%) of PQO.

Example 13

Preparation of DLS-base with a Catalyst

To a solution of 52.9 ml (1.3 equiv) trifluoroacetic anhydride in 1.0 L of dry methylene chloride 47.5 g (1.3 equiv)

indole-3-carboxylic acid was added in portions within 15 minutes. The reaction mixture was cooled to 20-25° C. and after 5 minutes 48.5 g (0.27 mol) HQO and 0.33 g (1 mol %) 4-dimethylaminopyridine were added in one portion. The reaction mixture was heated to 30-35° C. and stirred for 2 hours, then 26.5 ml (0.7 equiv) trifluoroacetic anhydride was added. The reaction mixture was stirred for additional 2 hours, then diluted with 800 ml of 10% sodium carbonate. From the mixture methylene chloride was distilled off. The precipitated solid was filtered, washed with water (3×100 ml) and dried. Yield is 97%.

Crude Dolasetron base (84 g) was dissolved in isobutyl acetate (2.6 L) at 95-100° C. Charcoal (4.2 g) was added to the solution, and after 10 minutes of stirring it was filtered off, and washed with isobutyl acetate (0.26 L). The solution was evaporated under reduced pressure to obtain a residue weighing 0.5-0.6 kg, which allowed to cool to room temperature, and then further cooled in a fridge for overnight. The precipitated crystals were filtered off, washed with isobutyl acetate (2×50 ml), and dried overnight at 40° C. under reduced pressure. Yield was 88%.

Example 14

Preparation of DLS-base Without Catalyst

Indole-3-carboxylic acid (17.7 g, 1.1 equiv.) was added in portions to a solution of trifluoroacetic anhydride (20 ml, 1.4 equiv.) in a mixture toluene (360 ml) and trifluoroacetic acid (90 ml), at room temperature (20-25° C.), during 15 minutes. After 5-minutes of stirring, endo-5-hydroxy-8-azatricyclo [5.3.1.0$^{3,8}$]-undecan-10-one (18.12 g, 0.1 mol), was added in one portion. The reaction mixture heated to 30-35° C., the solid phase dissolved. The solution was stirred for 2 hours without external heating. The trifluoroacetic acid was removed by evaporation under reduced pressure until starting of crystallization. 10% of an aqueous solution of sodium carbonate (360 ml) was added, then toluene was removed by evaporation under reduced pressure. The precipitated Dolasetron base monohydrate was collected by filtration, washed with water (3×60 ml), and dried overnight at 40° C. under reduced pressure. The dry product was weighed as 33.63 g (98%).

The dried crude Dolasetron base was dissolved in isobutyl acetate (1 L) at 95-100° C. Charcoal (1.7 g) was added to the solution, and after 10 minutes of stirring it was filtered off, and washed with isobutyl acetate (0.1 L). The solution was evaporated under reduced pressure to obtain a residue weighing 0.20-0.25 kg, which allowed to cool to room temperature, and then further cooled in a fridge overnight. The precipitated crystals were filtered off, washed with isobutyl acetate (2×20 ml), and dried overnight at 40-45° C. under reduced pressure. Yield was 88%.

Example 15

Preparation of DLS-MsOH of Formula VIII

Methanesulfonic acid (2.85 ml, 1 equiv) was added to a stirred suspension of Dolasetron base (14.24 g, 43.9 mmol) in a mixture of acetone-water 95:5 (100 ml). The solid dissolved immediately, after some minutes the salt precipitated in crystalline form. The mixture was put into fridge, after 4 hours the salt was filtered off, washed with same solvent mixture (2×15 ml), dried overnight in an air-ventilated oven at 40° C. The yield was 15.63 g (81%).

Example 16

Preparation of PivAN

In a 100-ml flask HAN (1.6 g) was dissolved in methylene chloride (60 ml). The solution was cooled to 0-5° C. and mixed with 5 equiv (4.1 ml) of triethylamine and 5 equiv (3.6 ml) of pivaloyl chloride. The reaction mixture was stirred for 6 days at 20-25° C. The conversion was monitored by TLC (eluent: ethyl acetate). The reaction mixture was diluted with methylene chloride (30 ml), washed with water (2×60 ml). The combined organic phase was dried on sodium sulfate, evaporated to dryness on rotavapor at 40-45° C. The product is about 3.5 g of oil.

Example 17

Preparation of HQO from PivAN

In a 250-ml flask the crude PivAN (4.7 g, 13 mmol) was dissolved in THF (64 ml) and potassium tert-butoxide (2 g, 1.4 equiv) was added under stirring. The solution was heated to reflux for 2 hours, and 32 ml of THF was distilled off during this reflux period. The mixture was cooled to 20-25° C., diluted with water (20 ml), and the pH was adjusted to 1 with concentrated HCl. The rest of THF was distilled out, and the mixture was refluxed for 6 hours, then cooled to 20-25° C. The pH of the solution was adjusted to 12 by addition of solid sodium hydroxide under cooling. The basic solution was extracted with methylene chloride (5×40 ml). The combined organic phase was dried on sodium sulfate, and evaporated to dryness. The residue was 1 g of brownish solid.

The invention claimed is:

1. A crystalline 7-methoxycarbonyl-9-(methoxycarbonylmethyl)-3-[(tetrahydro-2H-pyran-2-yl)oxy]-9-azabicyclo [3.3.1]nonane (PAN) compound of the following formula,

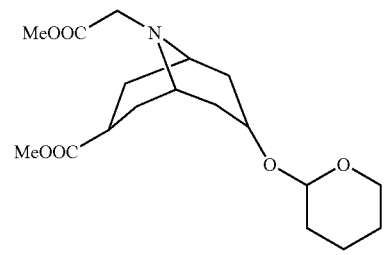

characterized by an XRD diffraction pattern having peaks at about 10.1, 15.3, and 18.2 degrees two-theta, ±0.2 degrees two-theta.

2. The crystalline PAN of claim 1, wherein the crystalline PAN is further characterized by the XRD diffraction pattern having peaks at about 10.1, 12.6, 13.4, 15.3, 18.2, 18.9, 19.2, 23.5, and 25.4 degrees two-theta, ±0.2 degrees two-theta.

3. The crystalline PAN of claim 2, wherein the crystalline PAN is characterized having a PXRD pattern as depicted in the PXRD illustrated by FIG. 7.

4. A quaternary ammonium salt of a 7-methoxycarbonyl-9-(methoxycarbonylmethyl)-3-[(tetrahydro-2H-pyran-2-yl) oxy]-9-azabicyclo[3.3.1]nonane compound (a PAN salt) of formula VIIs,

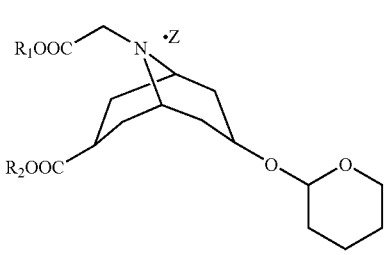

VIIs wherein $R_1$ and $R_2$ are methyl and Z is methanesulfonic acid (PAN-MsOH) and the quaternary ammonium salt is crystalline PAN-MsOH characterized by an XRD diffraction pattern having peaks at about 7.3, 11.6, and 14.6 degrees two-theta, ±0.2 degrees two-theta.

5. The quaternary ammonium salt of claim 4, wherein crystalline PAN-MsOH is further characterized by the XRD diffraction pattern having peaks at about 6.7, 12.5, 15.9, 17.1, 17.9, 19.0, 20.4, 22.2, and 23.8 degrees two-theta, ±0.2 degrees two-theta.

6. The quaternary ammonium salt of claim 5, wherein the crystalline PAN-MsOH is characterized having a PXRD pattern as depicted in FIG. 3.

7. An isolated endo-9-alkoxycarbonyl-5-[(tetrahydro-2H-pyran-2-yl)oxy]-8-azatricyclo[5.3.1.0$^{3,8}$]undecan-10-one compound (a PQO compound) of formula IX,

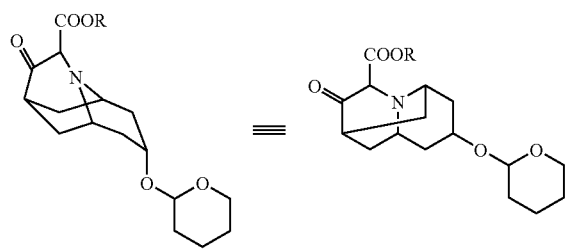

IX wherein R is a $C_{1-6}$ alkyl or a $C_{6-8}$ aryl.

8. The isolated compound of claim 7, wherein R is methyl (PQO).

9. The isolated compound of claim 8, wherein the isolated compound is crystalline PQO characterized by an XRD diffraction pattern having peaks at about 7.3, 14.7, and 17.2 degrees two-theta.

10. The isolated compound of claim 9, wherein crystalline PQO is further characterized by the XRD diffraction pattern having peaks at about 10.7, 15.3, 17.6, 18.2, and 21.4 degrees two-theta, ±0.2 degrees two-theta.

11. The isolated compound of claim 10, wherein the crystalline PQO is characterized having a PXRD pattern as depicted in FIG. 5.

12. A 7-alkoxycarbonyl-9-(alkoxycarbonylmethyl)-3-acyloxy-9-azabicyclo[3.3.1]nonane compound (a PivAN compound) of formula XIII

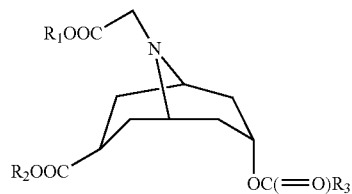

XIII wherein $R_1$, $R_2$ and $R_3$ are independently $C_{1-6}$ alkyl or $C_{6-8}$ aryl.

13. The compound of claim 12, wherein $R_1$ and $R_2$ are methyl and $R_3$ is tert-butyl.

14. A method of preparing a 7-methoxycarbonyl-9-(methoxycarbonylmethyl)-3-[(tetrahydro-2H-pyran-2-yl)oxy]-9-azabicyclo[3.3.1]nonane compound (a PAN compound) of formula VII, comprising

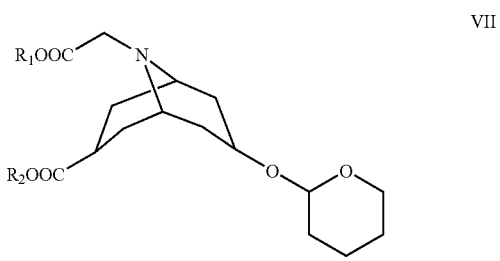

VII a) preparing a 7-alkoxycarbonyl-9-(alkoxycarbonylmethyl)-9-azabicyclo[3.3.1]nonane-3-ol compound (a HAN compound) of formula VI

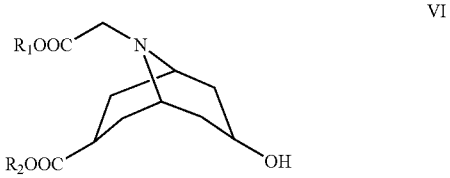

VI comprising combining an OAN compound of formula V

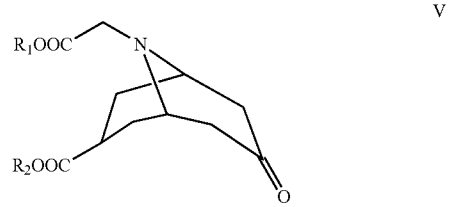

V or salts thereof, a reducing agent, and a solvent selected from the group consisting of water, water miscible organic solvents and mixtures thereof to form mixture to obtain an HAN compound of formula VI;

b) mixing the HAN compound of formula VI, an ether protecting group, an acid, and a $C_{3-8}$ ester to form a mixture; and c) adding a base to the mixture to obtain the PAN compound of formula VII, wherein $R_1$ and $R_2$ are independently a $C_{1-6}$ alkyl or a $C_{6-8}$ aryl.

15. The method of claim 14, wherein $R_1$ and $R_2$ are methyl.

16. The method of claim 14, wherein the ether protecting group is cyclic ether, the $C_{3-8}$ ester is ethylacetate, and the acid is methanesulfonic acid.

17. The method of claim 16, wherein the cyclic ether is tetrahydropyran.

18. The method of claim 14, wherein a solution of the acid in the $C_{3-8}$ ester is added drop-wise to a solution of the HAN compound and a substance comprising an ethereal protecting group at a temperature of about 30° C. to about 50° C.

19. The method of claim 18, wherein a PAN salt is recovered by a process of drying a precipitate obtained by adding drop-wise the solution of the acid in the $C_{3-8}$ ester to the solution comprising the HAN and the ether protecting group.

20. The method of claim 19, further comprising converting the PAN salt of formula VIIs to a Dolasetron (DLS) salt of formula VIIIs,

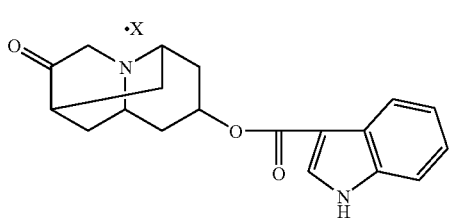

VIIIs wherein, X is an acid selected from the group consisting of: hydrochloric acid, hydrobromic acid, sulfuric acid, nitric acid, phosphoric acid, perchloric acid, fluoroboric acid, formic acid, acetic acid, propionic acid, trichloroacetic acetic, trifluoroacetic acid, maleic acid, fumaric acid, succinic acid, oxalic acid, tartaric acid, citric acid, mandelic acid, benzoic acid, salicylic acid, naphthalene carboxylic and dicarboxylic acids, methanesulfonic acid, ethanesulfonic acid, trifluoromethanesulfonic acid, p-toluenesulfonic acid, camphorsulfonic acid, benzenesulfonic acid, naphthalene sulfonic and disulfonic acids.

21. The method of claim 14, wherein the mixture in step b) is heated to a temperature of about 40° C. to about 60° C. for a period of about 15 minutes to about 1 hour.

22. The method of claim 21, wherein the heated mixture is cooled to a temperature of about 5° C. to about 20° C. for a period of about 1 to about 4 hours.

23. The method of claim 14, wherein the base is selected from the group consisting of sodium hydroxide, sodium carbonate, sodium bicarbonate, potassium hydroxide, potassium carbonate and potassium bicarbonate.

24. The method of claim 14, further comprising converting the PAN compound of formula VII to a Dolasetron (DLS) salt of formula VIIIs, wherein, X is an acid selected from the group consisting of hydrochloric acid, hydrobromic acid, sulfuric acid, nitric acid, phosphoric acid, perchloric acid, fluoroboric acid, formic acid, acetic acid, propionic acid, trichloroacetic acetic, trifluoroacetic acid, maleic acid, fumaric acid, succinic acid, oxalic acid, tartaric acid, citric acid, mandelic acid, benzoic acid, salicylic acid, naphthalene carboxylic and dicarboxylic acids, methanesulfonic acid, ethanesulfonic acid, trifluoromethanesulfonic acid, p-toluenesulfonic acid, camphorsulfonic acid, benzenesulfonic acid, naphthalene sulfonic and disulfonic acids.

25. The method of claim 14, and 30 to 32, further preparing an endo-9-alkoxycarbonyl-5-[(tetrahydro-2H-pyran-2-yl)oxy]-8-azatricyclo[5.3.1.0$^{3,8}$]undecan-10-one compound (a PQO compound) of formula IX,

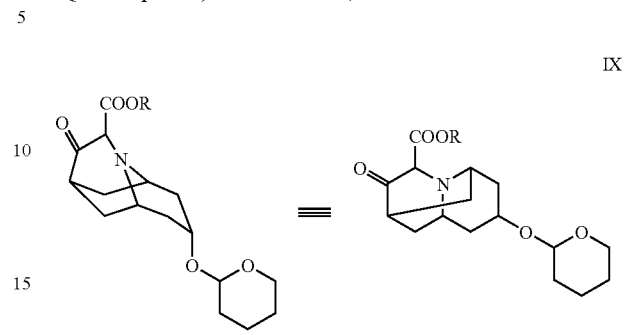

IX comprising
a) combining the PAN compound of formula VII

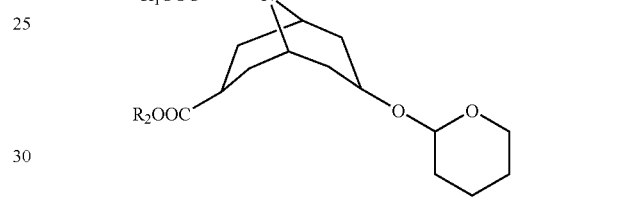

VII a metal alkoxide, and a polar aprotic organic solvent to form a mixture;
b) heating the mixture;
c) reacting the mixture of step b) with a weak acid forming a reaction mixture; and
d) adding a base to the reaction mixture of step c),
wherein R, $R_1$ and $R_2$ are a $C_{1-6}$ alkyl or $C_{6-8}$ aryl.

26. The method of claim 25, wherein R, $R_1$, and $R_2$ are methyl.

27. The method of claim 25, wherein the weak acid has a pKa of not less than 1, selected from the group consisting of formic acid, acetic acid, propionic acid, maleic acid, fumaric acid, succinic acid, oxalic acid, tartaric acid, citric acid, mandelic acid, benzoic acid, salicylic acid.

28. The method of claim 25, wherein the polar a-protic organic solvent is selected from the group consisting of $C_{2-8}$ ethers having a boiling point of about 60° C. to about 100° C., and wherein the metal alkoxide is selected from a group consisting of lithium alcoholates, sodium alcoholates and potassium alcoholates, and wherein the alcoholate moiety contains 1 to 4 carbons.

29. The method of claim 28, wherein the metal alkoxide is potassium tert-butoxide.

30. The method of claim 25, wherein the mixture of step a) is heated to a temperature of about 40° C. to about 120° C.

31. The method of claim 30, wherein the heated mixture is cooled to a temperature of about 0° C. to about 30° C., prior to the addition of the acid.

32. The method of claim 25, wherein the base is selected from the group consisting of sodium hydroxide, sodium carbonate, sodium bicarbonate, potassium hydroxide, potassium carbonate and potassium bicarbonate.

33. The method of claim 25, further comprising recovering the PQO compound of formula IX.

34. The method of claim 14, further preparing an endo-5-hydroxy-8-azatricyclo[5.3.1.0³,⁸]undecan-10-one salt (a HQO salt) of formula IIs

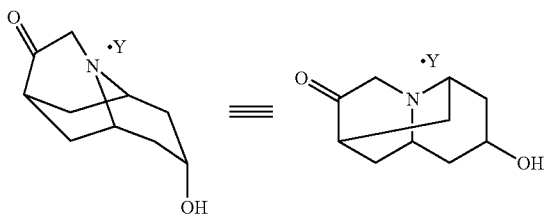

comprising
a) combining the PAN compound of formula VII,

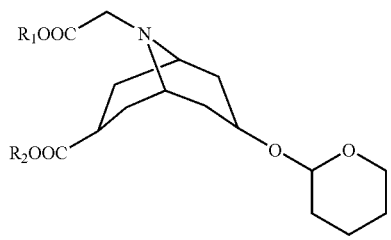

a metal alkoxide, and a polar aprotic organic solvent forming a mixture; and
b) adding to the mixture of step a) an acid selected from the group consisting of: hydrochloric acid, hydrobromic acid, sulfuric acid, nitric acid, phosphoric acid, and perchloric acid forming the HQO salt of formula IIs,
wherein, $R_1$ and $R_2$ are a $C_{1-6}$ alkyl or $C_{6-8}$ aryl, and Y is an acid selected from the group consisting of: hydrochloric acid, hydrobromic acid, sulfuric acid, nitric acid, phosphoric acid, and perchloric acid.

35. The method of claim 34, wherein $R_1$ and $R_2$ are methyl, and Y is HCl.

36. The method of claim 34, wherein the polar a-protic organic solvent is selected from the group consisting of $C_{2-8}$ ethers having a boiling point of about 60° C. to about 100° C., and wherein the metal alkoxide is selected from a group consisting of lithium alcoholates, sodium alcoholates and potassium alcoholates, and wherein the alcoholate moiety contains 1 to 4 carbons.

37. The method of claim 36, wherein the metal alkoxide is potassium tert-butoxide.

38. The method of claim 34, wherein the mixture in step a) is heated to a temperature of about 40° C. to about 120° C.

39. The method of claim 38, wherein the heated mixture is cooled to a temperature of about 0° C. to about 30° C., prior to the addition of the acid.

40. The method of claim 34, wherein the acid is either hydrochloric acid or camphorsulfonic acid.

41. The method of claim 34, further comprising adding a base, wherein a HQO compound of formula II is obtained.

42. The method of claim 41, wherein the base is selected from the group consisting of sodium hydroxide, sodium carbonate, sodium bicarbonate, potassium hydroxide, potassium carbonate and potassium bicarbonate.

43. The method of claim 41, further comprising combining HQO, an alcohol and an acid selected from the group consisting of: hydrochloric acid, hydrobromic acid, sulfuric acid, nitric acid, phosphoric acid, perchloric acid, fluoroboric acid, formic acid, acetic acid, propionic acid, trichloroacetic acid, trifluoroacetic acid, maleic acid, fumaric acid, succinic acid, oxalic acid, tartaric acid, citric acid, mandelic acid, benzoic acid, salicylic acid, naphthalene carboxylic and dicarboxylic acids, methanesulfonic acid, ethanesulfonic acid, trifluoromethanesulfonic acid, p-toluenesulfonic acid, benzenesulfonic acid, naphthalene sulfonic, and disulfonic acid forming a HQO salt of formula IIs.

44. The method of claim 43, wherein the alcohol is a $C_{1-4}$ alcohol.

45. The method of claim 43, wherein the acid is methanesulfonic acid.

46. The method of claim 43, further comprising adding a base, wherein the HQO compound of formula II is obtained as a purified compound.

47. The method of claim 41, further converting HQO of formula II to a DLS-salt of formula VIIIs comprising
a) forming a reaction mixture of HQO in an organic solvent;
b) mixing the reaction mixture with an anhydride, indole-3-carboxylic acid, an organic solvent, and a catalyst to form a mixture containing Dolasetron; and
c) reacting the mixture with an acid, to obtain the DLS-salt of formula VIIIs.

48. The method of claim 47, wherein the organic solvent is dichloromethane.

49. The method of claim 47, wherein HQO and the catalyst are added at the same time to a solution of the anhydride, the organic solvent and the 3-indole-carboxylic acid, providing the reaction mixture.

50. The method of claim 49, wherein the reaction mixture is heated to a temperature of about 25° C. to about 40° C. for a period of about 2 to about 18 hours, providing Dolasetron base.

51. The method of claim 47, wherein the acid is methanesulfonic acid.

52. A method of preparing a Dolasetron salt (a DLS-salt) of formula VIIIs

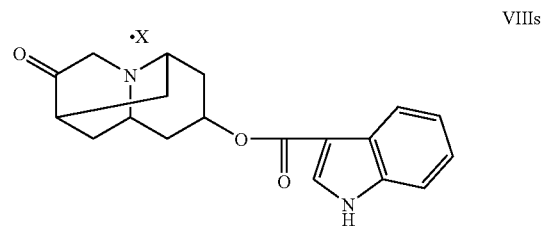

comprising
a) combining a CCA-ester of formula III,

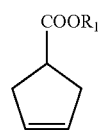

an oxidizing agent selected from the group consisting of: hydroperoxides, dialkyl peroxides, peroxyacids, peroxyes ters, diacyl peroxides, persulphate, perborate and perphosphate, a catalyst and a solvent selected from the group consisting of water, water miscible organic solvents and mixtures thereof forming a first intermediate mixture containing a CCA epoxide of formula IV

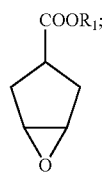

b) adding an oxidizing agent, a solvent selected from the group consisting of water and water miscible organic solvent to the forming a first intermediate mixture of the CCA epoxide of formula IV forming a second intermediate mixture;
c) raising the pH of the second intermediate mixture;
d) reacting the products in the second intermediate mixture with a pH 4 buffer, a glycine $C_{1-4}$ ester or salts thereof, and a substance comprising a carbonyl moiety selected from the group consisting of 1,3-acetonedicarboxylic acids, acetone and a $C_{1-4}$ ester thereof forming a third intermediate mixture containing an OAN compound of formula V

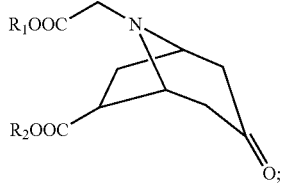

e) adding to the third intermediate mixture of the OAN compound of formula V a reducing agent, and a solvent selected from the group consisting of water, water miscible organic solvents and mixtures thereof forming a fourth intermediate mixture containing an HAN compound of formula VI

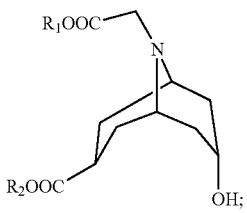

f) mixing the fourth intermediate mixture of the HAN compound of formula VI with a substance comprising an ether protecting group, an acid, and a $C_{3-8}$ ester forming a fifth intermediate mixture;

g) adding a base to the fifth intermediate mixture to obtain a PAN compound of formula VII

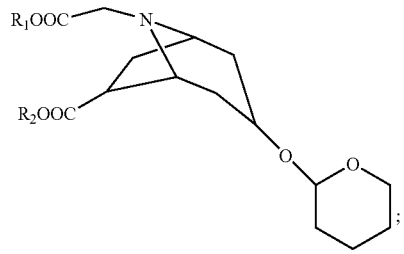

h) further combining the fifth intermediate mixture of the PAN compound of formula VII with a metal alkoxide and a polar aprotic organic solvent forming a sixth intermediate mixture;
i) heating the sixth intermediate mixture;
j) adding to the sixth intermediate mixture an acid selected from the group consisting of: hydrobromic acid, sulfuric acid, nitric acid, phosphoric acid, and perchloric acid forming a seventh intermediate mixture containing the HQO compound of formula II or a salt thereof of formula IIs

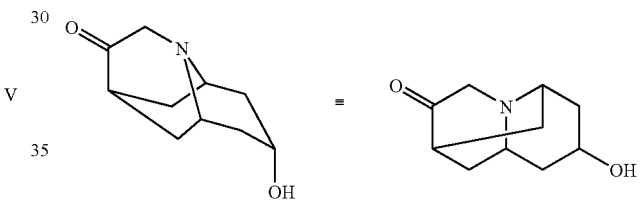

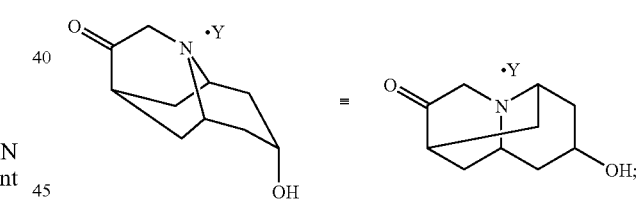

k) adding a base to the seventh intermediate mixture of the HQO compound of formula II or salt thereof of formula IIs;
l) further mixing with the seventh intermediate mixture an anhydride, 3-indole carboxylic acid, an organic solvent, and a catalyst; and
m) reacting the product of step l) with an acid to obtain the DLS-salt of formula VIIIs.

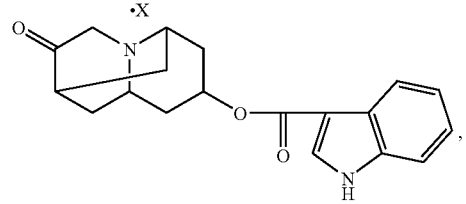

wherein $R_1$ and $R_2$ are each independently a $C_{1-6}$ alkyl or a $C_{6-8}$ aryl, and X and Y are each independently an acid selected from the group consisting of: hydrochloric acid, hydrobromic acid, propionic acid, trichloroacetic acetic, trifluoroacetic acid, maleic acid, fumaric acid, succinic acid, oxalic acid, tartaric acid, citric acid, mandelic acid, benzoic acid, salicylic acid, naphthalene carboxylic and dicarboxylic acid, methanesulfonic acid, ethanesulfonic acid, trifluoromethanesulfonic acid, p-toluenesulfonic acid, camphorsulfonic acid, benzenesulfonic acid, naphthalene sulfonic and disulfonic acids, preferably, methane sulfonic acid.

53. A method of preparing a 7-alkoxycarbonyl-9-(alkoxycarbonylmethyl)-3-acyloxy-9-azabicyclo[3.3.1]nonane compound (a PivAN compound) of formula XIII

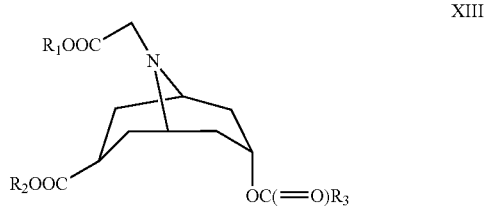

XIII comprising combining a HAN compound of formula VI,

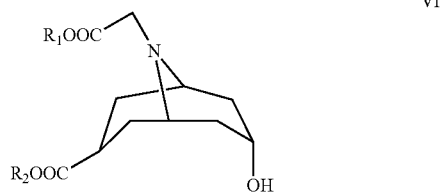

VI an acylating agent selected from a group consisting of: carboxylic acid, carboxylic halogenides, carboxylic anhydrides, a base, and a solvent selected from a group consisting of a-protic organic solvents and mixtures thereof forming a mixture to obtain the PivAN compound of formula XIII; wherein, $R_1$ and $R_2$ and $R_3$ are independently a $C_{1-6}$ alkyl or a $C_{6-8}$ aryl.

54. The method of claim 53, wherein $R_1$ and $R_2$ are methyl and $R_3$ is tert-butyl.

55. The method of claim 53, wherein the a-protic organic solvent is selected from the group consisting of a $C_{1-8}$ halogenated hydrocarbon, a $C_{2-8}$ ester, a $C_{2-8}$ ether, a $C_{3-6}$ ketone, a $C_{6-8}$ aromatic hydrocarbon, a $C_{3-10}$ amide, and mixtures thereof.

56. The method of claim 55, wherein the $C_{1-8}$ halogenated hydrocarbon is methylene chloride.

57. The method of claim 53, wherein the HAN compound and the solvent are combined first to form a solution which solution is cooled to a temperature of about $-5°$ C. to about $15°$ C. prior to the addition of the base and of the acylating agent.

58. The method of claim 53, wherein the base is selected from a group consisting sodium hydroxide, sodium carbonate, sodium bicarbonate, potassium hydroxide, potassium carbonate and potassium bicarbonate, trialkyl amines, and an N-containing heterocycle, wherein the acetylating agent is an acyl halogenide.

59. The method of claim 58, wherein the acetylating agent is pivaloyl chloride.

60. The method of claim 53, wherein the addition of the base and of the acylating agent to the HAN compound and the solvent provides a mixture which is maintained at a temperature of about 0° C. to about 80° C. for a period of about 1 day to about 20 days.

61. The method of claim 53, further comprising converting the PivAN compound of formula XIII to a Dolasetron (DLS) salt of formula VIIIs, wherein, X is an acid selected from the group consisting of: hydrochloric acid, hydrobromic acid, sulfuric acid, nitric acid, phosphoric acid, perchloric acid, fluoroboric acid, formic acid, acetic acid, propionic acid, trichloroacetic acetic, trifluoroacetic acid, maleic acid, fumaric acid, succinic acid, oxalic acid, tartaric acid, citric acid, mandelic acid, benzoic acid, salicylic acid, naphthalene carboxylic and dicarboxylic acids, methanesulfonic acid, ethanesulfonic acid, trifluoromethanesulfonic acid, p-toluenesulfonic acid, camphorsulfonic acid, benzenesulfonic acid, naphthalene sulfonic and disulfonic acids.

62. A method of preparing the compound endo-5-hydroxy-8-azatricyclo[5.3.1.0$^{3,8}$]undecan-10-one (HQO) of formula II

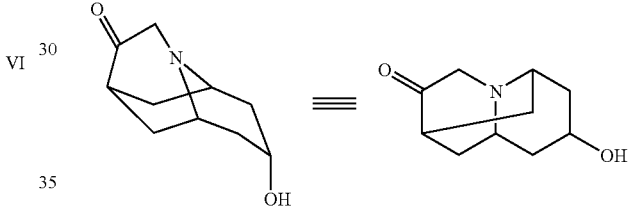

II comprising a) combining a PivAN compound of formula XIII,

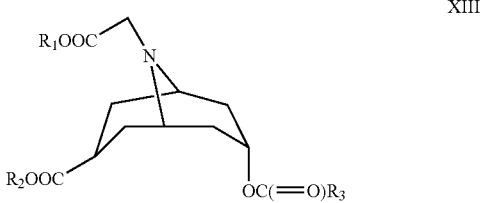

XIII a metal alkoxide, and a polar aprotic organic solvent forming a mixture;

b) heating the mixture; and c) adding to the mixture an acid selected from the group consisting of a hydrochloric acid, hydrobromic acid, sulfuric acid, nitric acid, phosphoric acid, and perchloric acid forming the HQO compound.

63. The method of claim 62, wherein $R_1$ and $R_2$ are methyl and $R_3$ is tert-butyl.

64. The method of claim 62, wherein the acid in step c) is HCl or camphorsulfonic acid.

65. The method of claim 62, wherein the polar a-protic organic solvent is selected from the group consisting of a $C_{2-8}$ ether having a boiling point of about 60° C. to about 100° C., and wherein the metal alkoxide is selected from the group consisting of lithium alcoholates, sodium alcoholates and potassium alcoholate; wherein the alcoholate moiety contains 1 to 4 carbons.

66. The method of claim 65, wherein the PivAN compound of formula XIII is dissolved in the polar a-protic organic solvent prior to adding the metal alkoxide.

67. The method of claim 65, wherein the metal alkoxide is potassium tert-butoxide.

68. The method of claim 62, wherein combining the PivAN compound of formula XIII, the polar a-protic organic solvent and the metal alkoxide forms a reaction mixture, which is heated to a temperature of about 40° C. to about 120° C. for a period of about 0.5 hours to about 8 hours.

69. The method of claim 68, wherein the heated mixture is cooled to a temperature of about 0° C. to about 30° C.

70. The method of claim 69, wherein prior to the addition of the acid, a solvent selected from the group consisting of water, water immiscible organic solvents and mixtures thereof is combined with the cooled reaction mixture.

71. The method of claim 70, wherein the acidic mixture is heated to about the reflux temperature for a period of about 3 hours to about 24 hours.

72. The method of claim 71, further comprising a step of recovering HQO of formula II wherein the heated mixture is cooled to a temperature of about 0° C. to about 30° C., adding a base, extracting the product with water immiscible organic solvent, and evaporating the water immiscible organic solvent.

73. The method of claim 72, wherein a base selected from a group consisting of sodium hydroxide, sodium carbonate, sodium bicarbonate, potassium hydroxide, potassium carbonate and potassium bicarbonate is added to the cooled acidic mixture.

74. The method of claim 72, wherein the water immiscible organic solvent is selected from the group consisting of $C_{2-8}$ esters, linear, branched or cyclic $C_{2-8}$ ethers, $C_{3-6}$ ketones and $C_{5-8}$ aliphatic hydrocarbons, and $C_{1-8}$ halogenated hydrocarbons.

75. The method of claim 62, further converting HQO of formula II to a DLS-salt of formula VIIIs comprising
a) forming a reaction mixture of HQO in an organic solvent;
b) mixing the reaction mixture with an anhydride, indole-3-carboxylic acid, an organic solvent, and a catalyst to form a mixture containing Dolasetron; and
c) reacting the mixture with an acid, to obtain the DLS-salt of formula VIIIs.

76. The method of claim 75, wherein the organic solvent is dichloromethane.

77. The method of claim 75, wherein HQO and the catalyst are added at the same time to a solution of the anhydride, the organic solvent and the 3-indole-carboxylic acid, providing the reaction mixture.

78. The method of claim 77, wherein the reaction mixture is heated to a temperature of about 25° C. to about 40° C. for a period of about 2 to about 18 hours, providing Dolasetron base.

79. The method of claim 75, wherein the acid is methanesulfonic acid.

80. A method of preparing a Dolasetron salt (a DLS-salt) of formula VIIIs

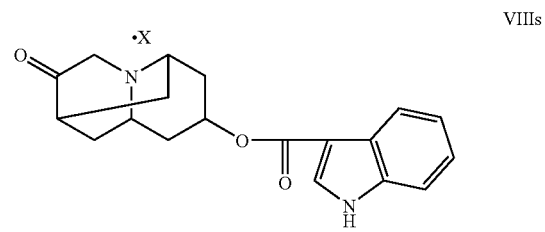

comprising
a) combining a CCA-ester of formula III,

an oxidizing agent selected from the group consisting of: hydroperoxides, dialkyl peroxides, peroxyacids, peroxyesters, diacyl peroxides, persulphate, perborate and perphosphate, a catalyst and a solvent selected from the group consisting of water, water miscible organic solvents and mixtures thereof forming a first intermediate mixture containing a CCA epoxide of formula IV

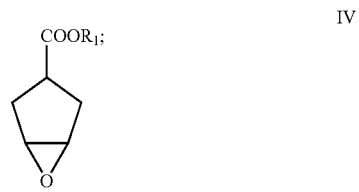

b) adding to the first intermediate mixture of the CCA epoxide of formula IV an oxidizing agent, and a solvent selected from the group consisting of water and water miscible organic solvent to form a second intermediate mixture;
c) raising the pH of the second intermediate mixture;
d) reacting the products in the second intermediate mixture with a pH 4 buffer, a glycine $C_{1-4}$ ester or salts thereof, and a substance comprising a carbonyl moiety selected from the group consisting of 1,3 acetonedicarboxylic acids, acetone and a $C_{1-4}$ ester thereof to form a third intermediate mixture; containing an OAN compound of formula V

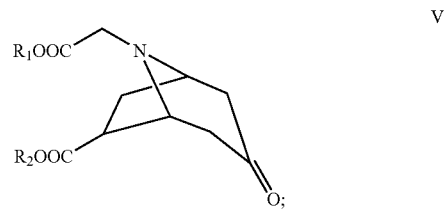

e) adding to the third intermediate mixture of the OAN compound of formula V a reducing agent, and a solvent selected from the group consisting of water, water miscible organic solvents and mixtures thereof to form a fourth intermediate mixture containing an HAN compound of formula VI

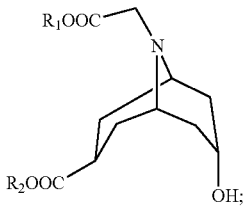

VI f) adding to the fourth intermediate mixture of the HAN compound of formula VI an acylating agent selected from the group consisting of: carboxylic acid, carboxylic halogenides, carboxylic anhydrides, a base, and a solvent selected from the group consisting of aprotic organic solvents and mixtures thereof to form a fifth intermediate mixture containing a PivAN compound of formula XIII

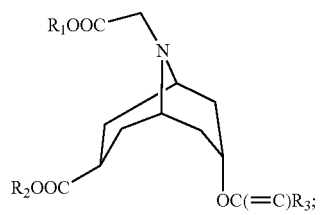

XIII g) adding to the fifth intermediate mixture of the PivAN compound of formula XIII a metal alkoxide, and a polar aprotic organic solvent to form a sixth intermediate mixture;

h) heating the sixth intermediate mixture, and adding an acid selected from the group consisting of hydrochloric acid, hydrobromic acid, sulfuric acid, nitric acid, phosphoric acid, and perchloric acid to form a seventh intermediate mixture containing the HQO compound of formula II

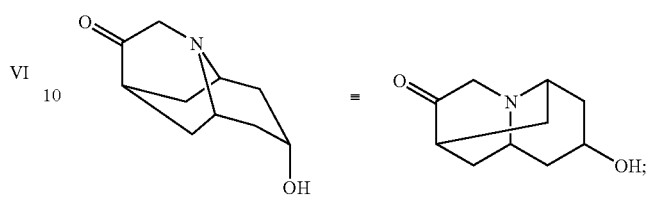

II i) mixing the seventh intermediate mixture of the HQO compound of formula II with an anhydride, 3-indole carboxylic acid, an organic solvent, and a catalyst; and j) reacting the product of step i) with an acid to obtain the DLS-salt of formula VIIIs

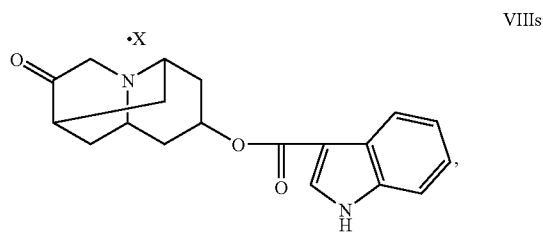

VIIIs wherein $R_1$, $R_2$, and $R_3$ are each independently a $C_{1-6}$ alkyl or a $C_{6-8}$ aryl, and X is an acid selected from the group consisting of hydrochloric acid, hydrobromic acid, sulfuric acid, nitric acid, phosphoric acid, perchloric acid, fluoroboric acid, formic acid, acetic acid, propionic acid, trichloroacetic acetic, trifluoroacetic acid, nialeic acid, fumaric acid, succinic acid, oxalic acid, tartaric acid, citric acid, mandelic acid, benzoic acid, salicylic acid, naphthalene carboxylic and dicarboxylic acids, methanesulfonic acid, ethanesulfonic acid, trifluoromethanesulfonic acid, p-toluenesulfonic acid, camphorsulfonic acid, benzenesulfonic acid, naphthalene sulfonic and disulfonic acids, preferably, methane sulfonic acid.

* * * * *